(12) United States Patent
Zhang

(10) Patent No.: US 10,709,327 B2
(45) Date of Patent: Jul. 14, 2020

(54) THIN FILM ANALYSIS APPARATUS AND METHOD FOR A CURVED SURFACE

(71) Applicant: Aizhong Zhang, Rochester, NY (US)

(72) Inventor: Aizhong Zhang, Rochester, NY (US)

( * ) Notice: Subject to any disclaimer, the term of this patent is extended or adjusted under 35 U.S.C. 154(b) by 0 days.

(21) Appl. No.: 16/209,873

(22) Filed: Dec. 4, 2018

(65) Prior Publication Data

US 2019/0183332 A1 Jun. 20, 2019

Related U.S. Application Data

(60) Provisional application No. 62/607,778, filed on Dec. 19, 2017.

(51) Int. Cl.
*G01N 21/21* (2006.01)
*A61B 3/10* (2006.01)
(Continued)

(52) U.S. Cl.
CPC ............ *A61B 3/101* (2013.01); *A61B 3/0025* (2013.01); *A61B 3/152* (2013.01);
(Continued)

(58) Field of Classification Search
CPC ........... G01N 2021/213; G01N 21/956; G01N 33/54366; G01N 33/54373; G01N 21/21; G01N 21/4788; G01N 33/54386; G01N 2021/202; G01N 21/4133; G01N 21/55; G01N 21/553; G01N 21/8422;
(Continued)

(56) References Cited

U.S. PATENT DOCUMENTS 3,985,447 A   10/1976 Aspnes
4,647,207 A    3/1987 Bjork
(Continued)

OTHER PUBLICATIONS

Zhang, Aizhong, Gheorghe Salahura, Ranjini Kottaiyan, Geunyoung Yoon, James V. Aquavella, and James M. Zavislan. "Multimodal imaging of ocular surface of dry eye subjects." In Multimodal Biomedical Imaging XI, vol. 9701, p. 97010H. International Society for Optics and Photonics, 2016.
(Continued)

*Primary Examiner* — Michael P Stafira
(74) *Attorney, Agent, or Firm* — Lynne M. Blank, Esq

(57) ABSTRACT

A thin film analysis apparatus and method for a curved surface is disclosed. The apparatus includes an illuminator, a sample, an imaging group, one or more beamsplitters, optional focusing groups, polarization analyzers, detectors and optional display and analysis systems. The image series are recorded, preferably substantially synchronously. The system can be calibrated by as few as one reference phantom that has the same or substantially similar geometry as the sample under test. Based on calibration, a lookup table of the effective reflectance can be created, which is proportional to the portion of the light that reaches the detectors, or the mutual subtraction of the effective reflectance values of all possible combinations of the unknown optical parameters within certain search ranges of the sample. The experimentally measured results are compared with the lookup table, and optical properties, for example, the thicknesses and refractive indices of the thin film can be determined.

19 Claims, 13 Drawing Sheets

(51) Int. Cl.
   *A61B 3/15* (2006.01)
   *A61B 3/00* (2006.01)
   *G01B 11/06* (2006.01)
   *G02B 27/14* (2006.01)
   *G01N 21/41* (2006.01)
   *G01N 21/84* (2006.01)

(52) U.S. Cl.
   CPC ...... *G01B 11/0625* (2013.01); *G01B 11/0641* (2013.01); *G01N 21/211* (2013.01); *G01N 21/4133* (2013.01); *G01N 21/8422* (2013.01); *G02B 27/14* (2013.01); *G01N 2021/8427* (2013.01)

(58) Field of Classification Search
   CPC ......... G01N 21/9501; G01N 21/95684; G01N 33/526; G01N 33/551; G01N 33/552; G01N 33/56927; G01N 2021/8822; G01N 21/95607; G01N 2021/1731; G01N 2021/214; G01N 2021/7723; G01N 2021/773; G01N 2021/7773; G01N 2021/7779; G01N 2021/7783; G01N 2021/7793; G01N 2021/7796; G01N 21/1717; G01N 21/45; G01N 21/4738; G01N 21/636; G01N 21/6428; G01N 21/78; G01N 33/0054; G01N 33/56911; G01N 33/56944; G01N 33/56983; G01N 33/56988; G01N 15/1475; G01N 2015/1479; G01N 2015/1497; G01N 21/23; G01N 21/554; G01N 21/6458; G01N 21/658; G01N 21/94; G01N 2333/135; G01N 2333/162; G01N 2333/22; G01N 2333/295; G01N 2333/315; G01N 33/02; G01N 33/493; G01N 33/543; G01N 33/547; G01B 11/065; G01B 11/303; G01B 11/0616; G01B 11/0641; G01B 11/0625; G01B 2210/56; G01B 2290/30; G01B 2290/65; G01B 2290/70; G01B 9/02002; G01B 9/02004; G01B 9/02007; G01B 9/02072; G01J 3/0286; G01J 3/10; G01J 3/36; G01J 5/38; G01J 5/60; G01J 3/02; G01J 3/0208; G01J 3/12; G01J 3/42; G01J 4/00; G01J 4/04; G02B 21/361; G02B 26/0833; G02B 5/28; G02B 5/3016
   See application file for complete search history.

(56) References Cited

U.S. PATENT DOCUMENTS

| | | | |
|---|---|---|---|
| 4,653,924 A | 3/1987 | Itonaga | |
| 4,957,368 A | 9/1990 | Smith | |
| 5,061,072 A | 10/1991 | Folkard | |
| 5,120,966 A | 6/1992 | Kondo | |
| 5,166,752 A | 11/1992 | Spanier | |
| 5,335,066 A * | 8/1994 | Yamada | G01N 21/211 356/364 |
| 5,438,415 A * | 8/1995 | Kazama | G01B 11/065 356/367 |
| 5,835,220 A * | 11/1998 | Kazama | G01J 4/04 356/369 |
| 6,236,459 B1 | 5/2001 | Negahdaripour | |
| 6,278,519 B1 | 8/2001 | Rosencwaig | |
| 7,067,818 B2 | 6/2006 | Harrison | |
| 7,121,666 B2 | 10/2006 | Tseng | |
| 7,126,131 B2 | 10/2006 | Harrison | |
| 9,615,735 B2 | 4/2017 | Huang | |
| 9,642,520 B2 | 5/2017 | Korb | |
| 9,693,682 B2 | 7/2017 | Korb | |

OTHER PUBLICATIONS

Lee, Kan Yan, and Yu Faye Chao. "The ellipsometric measurements of a curved surface." Japanese journal of applied physics 44, No. 7L (2005): L1015.

Han, Chien-Yuan, Zhen-You Lee, and Yu-Faye Chao. "Determining thickness of films on a curved substrate by use of ellipsometric measurements." Applied optics 48, No. 17 (2009): 3139-3143.

Li, Weiqi, Hao Jiang, Chuanwei Zhang, Xiuguo Chen, Honggang Gu, and Shiyuan Liu. "Characterization of curved surface layer by Mueller matrix ellipsometry." Journal of Vacuum Science & Technology B, Nanotechnology and Microelectronics: Materials, Processing, Measurement, and Phenomena 34, No. 2 (2016): 020602.

\* cited by examiner

THIN FILM ANALYSIS APPARATUS AND METHOD FOR A CURVED SURFACE

CROSS REFERENCE TO RELATED APPLICATIONS

Priority is claimed to Provisional U.S. Patent Application Ser. No. 62/607,778 by A. Zhang filed Dec. 19, 2017 and entitled "Thin Film Analysis Apparatus and Method for a Curved Surface", the disclosure of which is incorporated herein by reference.

FIELD OF THE INVENTION

This invention relates to the field of thin film coating metrology. In particular, this invention relates to thin film coating thickness and/or refractive index measurement apparatus and method for a curved surface by means of a generalized ellipsometric technique. The thin film coating could be dynamic or static, single-layered or multiple-layered.

BACKGROUND OF THE INVENTION

Various optical techniques have been developed to measure a thin film coating on a substrate in the prior art. These optical techniques provide non-invasive means to characterize various types of thin films widely used in industry and academia. These techniques usually involve measurements of the irradiance and/or the polarization of the transmitted and reflected light from the sample under test. Common thin film measurement techniques include but are not limited to monochromatic reflectometry, spectral reflectometry, and ellipsometry.

In the method of monochromatic reflectometry, light is reflected off a sample, and the irradiances of both the incident and reflected beams are measured. The light spectrum is concentrated around a single wavelength, such as the light from a narrow bandwidth laser source. The incident light is of known polarization, which could be completely unpolarized or fully polarized, or some other known polarization state. With the known wavelength, known incident angle, and known refractive indices of the substrate and optionally the refractive index of the thin film coating, optical properties of the thin film coating, including the thickness and/or the refractive index of the thin film coating, can be determined.

In the method of spectral reflectometry, including spectrophotometry, various wavelengths are employed. One common setup of spectral reflectometry is to have a light source with variable wavelength, and change the light source wavelength in time series, and maintain the detector to be the same, as long as the detector is responsive to all the variable wavelengths. Another common setup of spectral reflectometry is to use a broadband light source, such as a white light source to directly illuminate the sample, and at the detector side, a spectrometer is used to direct light components of different wavelengths into different spectral channels. The irradiance reflectance of each wavelength is analyzed, and optical properties of the thin film coating could be calculated. Some spectral reflectometers are described in U.S. Pat. Nos. 7,126,131, 7,067,818 and 5,120,966, all incorporated by reference herein in their entirety.

Further, new methods in spectral reflectometry for application in ophthalmology are disclosed in the prior art, where the spectral reflection or reflected color as a result of the tear film interference is analyzed to retrieve optical thickness values. For example, U.S. Pat. No. 7,121,666, incorporated herein by reference in its entirety, describes a system that analyzes the lipid layer thickness, by comparing the dominant color of acquired image with a look up table, and the look up table is a simulation of color based on the setup in the patent. Also, U.S. Pat. Nos. 9,693,682 and 9,642,520, incorporated herein by reference in their entirety, describe a system that analyzes the tear film thickness. The system compares the RGB color of each pixel of acquired data with a tear film layer thickness (TFLT) palette, which is generated from theoretical optical wave interference model of the ocular surface, such as the air/$SiO_2$/$MgF_2$ or air/$SiO_2$/$MgF_2$/$SiO_2$ model, or models with the refractive index and wavelength dispersion values of biological materials. The corresponding lipid layer thickness values are determined from the closest matching color in the TFLT palette. The thickness result accuracy in these patents is highly dependent on the accuracy of the theoretical model.

Furthermore, in U.S. Pat. No. 6,236,459, incorporated herein by reference in its entirety, a spectral reflectometric method with a plurality of wavelength filters for thin film analysis is described. A plurality of thin films with substantially predetermined intensity and spectral characteristics are used for calibration, and a look-up table comprising the data from a plurality of calibration thin films were used to enable accurate determination of the thin film thickness. Weight vectors based on orthogonal polynomials, such as normalized Legendre polynomials, are calculated in order to analyze the thin film thickness. This complicated calibration and analysis process requires precise fabrication and testing of a plurality of calibration thin films, and intensive mathematical calculation of weight vectors.

In the method of ellipsometry, the polarization states of the light before and after reflection or transmission of a sample are measured. The incident light can be monochromatic or broadband. Usually, polarizers, quarter-wave plates, or some other compensators are employed in the optical path. The incident angle and the wavelength spectrum of the light are properly chosen, and the orientation directions of the polarization elements are precisely controlled or rotated, so that the change in the polarization state of the beam could be measured. The change in polarization is characterized in both amplitude and phase changes, and they are very sensitive to the thickness and refractive index of the thin films. In the prior art of ellipsometers, two types are commonly seen, the rotating null ellipsometer and the rotating analyzer ellipsometer. Some types of ellipsometry methods or apparatuses are described in U.S. Pat. Nos. 5,166,752, 5,061,072, 4,957,368, 4,653,924, 4,647,207, and 3,985,447, all incorporated herein by reference in their entirety.

Conventionally, ellipsometry was limited to measure flat surfaces, and in recent years, several methods have been developed to apply ellipsometry on curved surfaces. Chao et al described a method of determining thickness of films on a curved substrate by a three-intensity measurement technique in "*The ellipsometric measurements of a curved surface.*" Japanese Journal of Applied Physics 44, no. 7L (2005), and "*Determining thickness of films on a curved substrate by use of ellipsometric measurements.*" Applied Optics 48, no. 17 (2009), incorporated herein by reference in their entirety. Furthermore, Li et al characterized a curved surface layer by Mueller matrix ellipsometry in "*Characterization of curved surface layer by Mueller matrix ellipsometry.*" Journal of Vacuum Science & Technology B, Nanotechnology and Microelectronics: Materials, Processing, Measurement, and Phenomena 34, no. 2 (2016), incorporated herein by reference in its entirety.

However, in the aforementioned prior art, these ellipsometric thin film measurement techniques are either limited to a flat sample, such as thin film coatings on a silicon wafer, or an approximately flat portion of a thin film coating on a curved substrate sample. For a curved surface, these techniques are either not applicable or only applicable to a very limited illuminated area of the measurement, where the region under investigation could be analyzed as a flat region. In some systems, an auxiliary focusing lens group is utilized to limit the illumination spot size to ensure the validity of the planar surface approximation of a small region on a curved surface.

Also, the prior art systems are limited to static coating, due to strict mounting constraints. Therefore, dynamic and fluidic coatings, such as the dynamically evolving lipid layer of a human tear film, anterior to a human eye, are generally not measurable with these techniques.

Further, to ensure a precise measurement with methods in the prior art, strict alignment requirements must be met. For example, the sample position has to be fixated and flat, the angles of incidence and reflection are precisely controlled, and the polarization elements precisely rotate at certain steps and to a certain position. Without a tight tolerance for alignment of these measurement systems in the prior art, the calculated thickness or refractive index values are not accurate, or even meaningless.

In some prior art systems, reference samples with known thin film coating thicknesses have been used for system calibration. For example, in U.S. Pat. No. 6,278,519, incorporated herein by reference in its entirety, a silicon substrate with an oxide layer of about 20 angstroms thickness is used for system calibration. However, these reference samples are also limited to planar or approximately planar samples.

Moreover, U.S. Pat. No. 9,615,735, incorporated herein by reference in its entirety, describes an optical coherence tomography system to measure the human tear film. However, that interferometer system requires a reference optical path to interfere the sample optical path with.

SUMMARY OF THE INVENTION

It is an object of this invention to extend the scope of ellipsometry to provide a method and apparatus to measure the thin film coating thickness and/or refractive index over a curved area, neither requiring the sample to be flat or near flat, nor requiring the sample to be static.

It is an object of this invention to provide a method and apparatus to measure an extended region of interest of the curved sample simultaneously without the need of a reference optical path in an interferometer. The region of interest covers an extended region of the curved surface, not just a limited region near the apex that can be approximated as a planar region or other small illuminated region.

It is another object of this invention to provide a thin film coating measurement apparatus that has a relaxed tolerance for alignment, which is essential to measure dynamically evolving thin films or samples difficult to remain static, such as the lipid layer of the tear film of a human eye, since there are always small-magnitude, involuntary movements of the human head and the eye.

It is another object of this invention to provide a simple yet effective process of calibration with as few as one appropriately chosen reference phantom sample (hereinafter also referred to as a reference phantom). The present calibration method is experimentally based on the reflectance data from a reference phantom sample, not merely based on a theoretical model.

It is yet another object of this invention to provide a thin film thickness or refractive index retrieval method that does not necessarily require color comparison of RGB three color channels simultaneously. The retrieval process of the recorded images from a sample is not determined by the dominant color or the closest matching color from a theoretical model. The basic thickness or refractive index retrieval method in this invention happens at each individual color channel One color channel would be sufficient to determine certain optical properties, such as thickness and/or refractive index in a small search range. Two or more color channels results could be compared to further enlarge the dynamic range and enhance accuracy, but simultaneous color comparison of color channels, such as the RGB three channels, is not necessary to determine the optical properties of the thin film.

It is still another object of this invention to provide an apparatus and method to measure not only a single-layer thin film coating on a substrate, but a multiple-layer thin film coating as well.

The present invention relates to a thin film analysis apparatus, comprising an illuminator for providing illumination light to an extended area of a sample, an imaging group to receive reflected light from an extended area of a sample, at least one non-polarizing beamsplitter to receive the reflected light from the imaging group and split the reflected light into more than one optical branch, at least two analyzers, one for receiving one of the optical branches from the beamsplitter and analyzing a polarization state thereof, wherein each of the analyzers is located between one of the beamsplitters and a detector; and at least two detectors, one for receiving one of the optical branches from one of the analyzers to generate and record image series of a surface of the extended area of the sample, wherein one detector is aligned uniquely with one of the at least two analyzers.

The invention also includes a method of analyzing a thin film over an extended area of a sample comprising the steps of illuminating an extended area of a sample having a geometrical shape with at least partially polarized illumination light, directing light reflected off the sample to pass through, in order, an imaging group, at least one non-polarizing beamsplitter, and at least two analyzers and at least two detectors, wherein one of the analyzers is uniquely aligned with one of the detectors, capturing and recording a sample image series with each of the detectors, differentiating the sample into different types, replacing the sample with a reference phantom with known optical properties, which has the same or substantially similar geometrical shape as of the sample or a segment of the sample to record an image series of the reference phantom with each of the detectors, calculating beamsplitter compensating factors due to an unequal splitting ratio and an unequal number of beamsplitters in different optical paths, selecting a search range for unknown optical parameters of the sample, calculating scaling factors based on the type of sample and a degree of polarization of the at least partially polarized illumination light, and determining the unknown optical parameters. A registration illumination system can also be included and located between the sample and the imaging group. When the registration illumination system is added, the method adds a step for aligning the image series of the detectors by matching a reflected image of the registration illumination system on each detector after capturing and recording the sample image series and a step for resizing the image series of the reference phantom to match the sample image series, based on the reflected images of the registration illumination system after replacing the sample with a reference phantom with known optical properties, which has the same or substantially similar geometrical shape as of the sample or a segment of the sample to record an image series of the reference phantom with each of the detectors. Preferably, the sample is differentiated into two sample types: Type 1 samples having a dominant reflection from a front surface, and no strong reflection from all other optical surfaces or structures beneath the front surface, and Type 2 samples having a transparent or semi-transparent front surface, with a depolarizing element beneath the front surface.

If the sample is a Type 1 sample under fully polarized illumination light, the method further comprises calculating scaling factors that quantify the proportionality of data numbers of the image series of the reference phantom and effective reflectances of the reference phantom, calculating effective reflectances of the sample, based on the scaling factors calculated from the reference phantom, creating a lookup table of effective reflectances of all possible combinations of the unknown optical parameters of the sample in the search range, comparing the effective reflectances of the sample with the lookup table, and selecting a set of optical parameters that generates the least discrepancy with the effective reflectances of the sample to determine the unknown parameters.

If the sample is a Type 1 sample under partially polarized illumination light, or a Type 2 sample under at least partially polarized illumination light, the method further comprises calculating scaling factors that quantify the proportionality of the mutual subtraction of data numbers of the image series of the reference phantom and the mutual subtraction of effective reflectances of the reference phantom, calculating the mutual subtraction of effective reflectances of the sample, based on the scaling factors calculated from the reference phantom, creating a lookup table of the mutual subtraction of effective reflectances of all possible combinations of the unknown optical parameters of the sample in the search range, comparing the mutual subtraction of the effective reflectances of the sample with the lookup table, and selecting a set of optical parameters that generates the least discrepancy with the mutual subtraction of the effective reflectances of the sample to determine the unknown parameters.

DETAILED DESCRIPTION OF THE INVENTION

Figure 1:
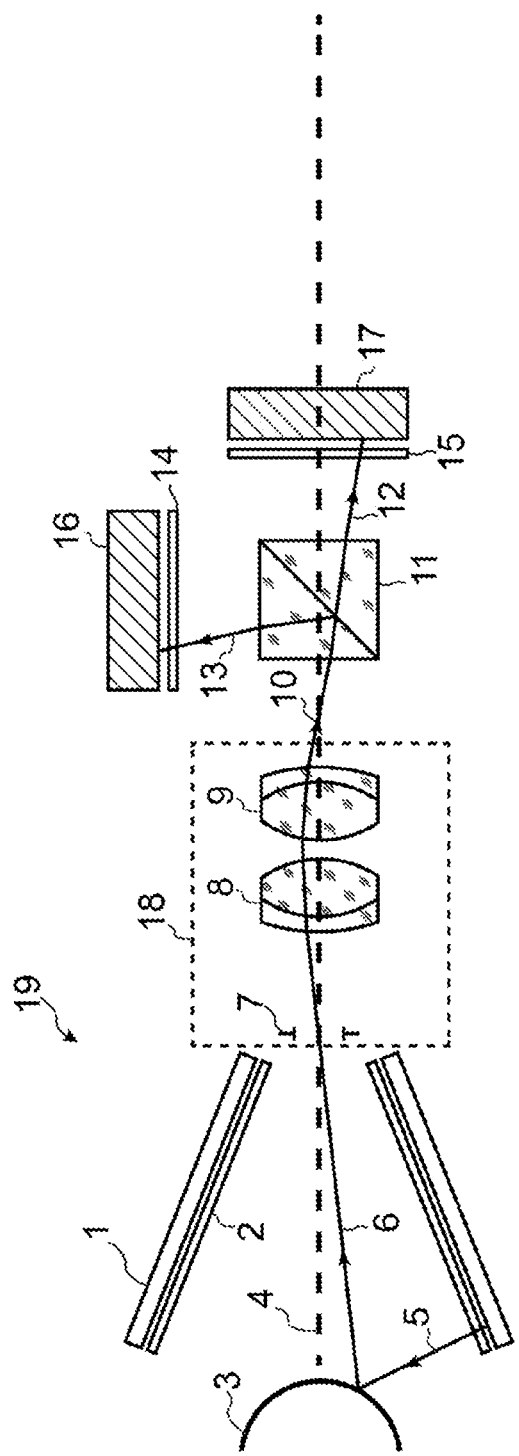
FIG. 1 is a preferred embodiment of a two-detector system.

The present invention involves a method and apparatus for measuring the thickness of a thin film coating on a curved substrate. The thin film coating must have a transmittance of larger than zero for the incident light.

The apparatus in this invention consists of an illuminator, a sample or a reference phantom sample on an adjustable support, an imaging group, one or more non-polarizing beamsplitters, optional focusing groups, two or more corresponding detector systems, and optional displays.

The illuminator preferably has an enclosed shape with one open end facing the sample and the other end with the imaging and detector system installed. Most preferably, the illuminator has rotational symmetry with the shape of a conical frustum, or a cylinder. The light source can be placed on the interior wall of the illuminator. The light source of the illuminator can be a broadband source, covering a plurality of wavelengths. The embodiment of the light source includes but is not limited to a panel of white light emitting diodes (LEDs) in the visible spectrum. One layer or several layers of diffusing materials can be placed in front of the light source, so that the output light is spatially more uniform. A polarizer structure can be placed in front of the diffusing layer(s) so that the light output is polarized. Preferably, the output light is circularly polarized. The light from the illuminator is directed toward the sample. The sample could be flat or curved and is preferably placed on a support to adjust its position to facilitate the alignment.

The calibration process is essential to the measurement accuracy of the present invention. A reference phantom sample can be used to calibrate the system. The reference phantom is preferably made of a material with known optical properties. It preferably has the same or at least similar radius of curvature as the sample under test. Preferably, the reflectance off the reference phantom should be close to the reflectance off the sample under test, so that a high dynamic range detector is not necessarily required.

The light reflected off a sample or a reference phantom is directed toward an imaging group. The imaging group design is preferred to be balanced with the design of the following imaging system so as to minimize the aberration of the final images on detectors.

After the light passes the imaging group, it goes through a beamsplitter system, and optionally another set of optical group, the focusing group, and then each branch reaches a detector system. If only beamsplitters that split input light into one transmitted light and the other reflected light are used, the total number of detector systems is always one greater than the total number of beamsplitters in the apparatus. If diffractive beamsplitters that split input light into multiple optical branches are used, there is at least one diffractive beamsplitter in the apparatus. The number of detectors could be two or more, as described hereinafter.

In one embodiment, a two-detector system, after the reflected light passes through an imaging group, it reaches a non-polarizing beamsplitter, and the light is split into two branches. The splitting ratio could be but is not limited to 50:50, and if the splitting is not even, this unequal splitting ratio should be taken into account, and during the subsequent data analysis, the irradiance data should be compensated accordingly based on the splitting ratio.

There is preferably one polarizer in front of each detector. The polarizer serves as a polarization analyzer, and possible embodiments of the analyzer include a linear polarizer or a circular polarizer. In a preferred embodiment of the two-detector system, the two polarizers are orthogonal to each other. More preferably, one polarizer is of the same polarization of the illumination light and the other is of the orthogonal polarization of the illumination light.

The two detector channels will enable the determination of up to two independent optical parameters of the thin film coating and the substrate.

If the thin film is coated on an optically thick substrate or if the substrate is absorptive or by some other means, there is no strong reflection from all other optical surfaces or structures beneath the front surface, only the reflection from the front surface is of concern. This type of sample will be referred to as the Type 1 sample herein. Further, if a Type 1 sample has a single-layer thin film coating on a known substrate, the two-detector system can measure both the thickness and refractive index of the thin film coating.

If the thin film is coated on the front surface of a substrate, and the substrate is transparent or semi-transparent, and there is a depolarizing element beneath the front surface, both the reflection from the front surface and the scattering from the depolarizing element are preferably taken into account. The embodiments of the depolarizing element include but are not limited to a roughened aluminum plate, a piece of paper, or a human iris. This type of sample will be referred to as the Type 2 sample herein. In the case of ocular surface tear film measurement, because of the physiological structure of the human iris, it can be modeled as a depolarizing scatterer. Therefore, the human eye can be treated as a Type 2 sample for tear film lipid layer analysis. Further, if a Type 2 sample has a single-layer thin film coating, the two-detector system can measure either the thickness or the refractive index of the thin film coating, given the other parameter is predetermined. The refractive indices at the average wavelengths of one or more detector color channels must be known in order to obtain precise thickness calculation. On the other hand, if the thickness of the thin film coating is known, the refractive indices of the coating material could be calculated based on the reflectance of the incident beam.

In another embodiment, a three-detector system, instead of only using one beamsplitter, two beamsplitters are used and the light is split into three different detector systems. Alternatively, the three optical branches can be generated with one diffractive beamsplitter with three main diffraction orders in use. Each optical branch passes an imaging group and an optional focusing group. Preferably, two of the polarizers in front of these three detectors are the same as those in the two-detector system: one is of the same polarization of the illumination light and the other is of the orthogonal polarization of the illumination light, and the third one is of another independent polarization. Possible unequal irradiance output values immediately after the beamsplitters should preferably be taken into account and be compensated appropriately in the image analysis. The extra detector and another independent polarization analyzer in a three-detector system would enable one more unknown optical parameter determination.

In yet another embodiment, a system with more than three detectors, similar to the case with three detectors, every time another detector is added with another independent polarizer, one more degree of freedom of the system can be characterized, and one more optical parameter could be measured. Following this methodology, a multiple-layer stack of thin film coating on a substrate could be measured and analyzed.

1. Description of the Embodiments

Referring to FIG. 1, a preferred embodiment of this invention is illustrated as the thin film analysis apparatus 19. FIG. 1 shows a two-detector system: illumination light from source 1 passes through a polarizer structure 2 to illuminate a sample 3. Sample 3 is preferably placed on a support (not shown in FIG. 1) to adjust the position. Incident illumination light 5 turns into light 6 after reflection, and it passes through an imaging group 18. Output light 10 goes through a beamsplitter 11, and light 10 is split into two channels 12 and 13. Light 12 goes through a polarizer 15 and reaches a detector 17, and in a similar manner, light 13 goes through a polarizer 14 and reaches a detector 16. In a preferred embodiment, real time images are displayed to help facilitate alignment and measurement monitoring. The recorded images or image series on detectors are optionally connected to a processor or a computer to be further analyzed.

Figure 4:
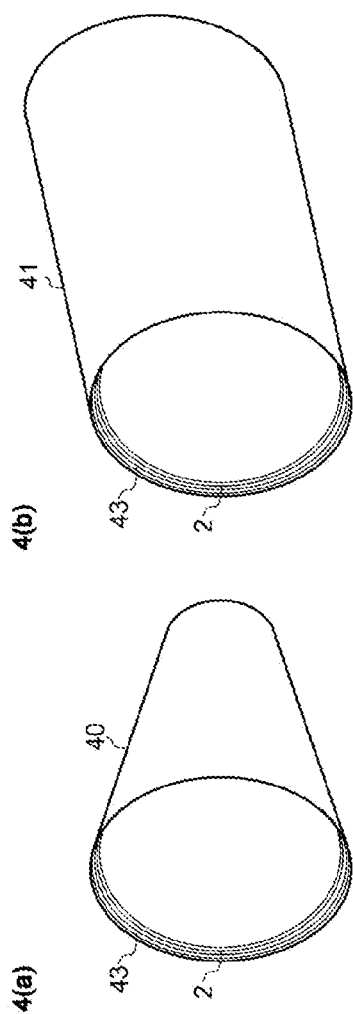
FIG. 4 illustrates two possible embodiments of the illuminator.

In a preferred embodiment, the illuminator shape has rotational symmetry. FIG. 4 illustrates two possible embodiments of the illuminator. In FIG. 4(a), the illuminator has the shape of a conical frustum 40. The interior of the illuminator includes an optional diffusing structure 43 and a polarizer structure 2. In FIG. 4(b), the illuminator has the shape of a cylinder 41.

Figure 5:
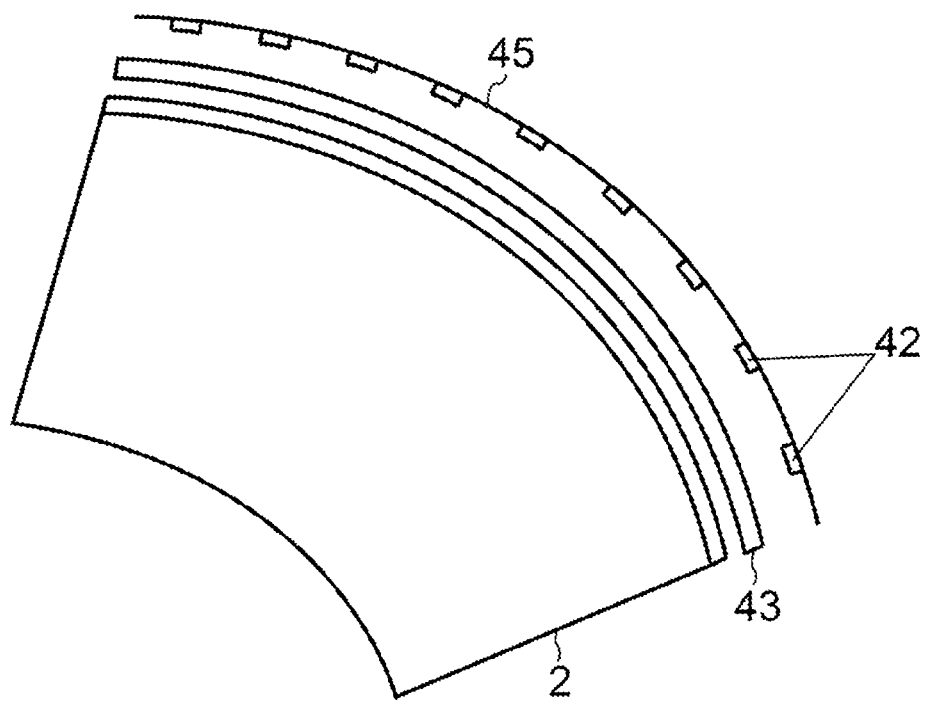
FIG. 5 illustrates the stratified layer structure of a portion of the illuminator.

FIG. 5 illustrates the detailed layer structure of a portion of the illuminator. In a preferred embodiment, these stratified layer structures are wrapped interiorly along the configuration of a rotationally symmetrical illuminator. An illuminator panel 45 has an array of individual broadband light sources 42. The embodiments of 42 include but are not limited to broadband light emitting diodes (LEDs), or white LEDs. Individual light sources 42 are placed on the interior wall of the illuminator panel 45. An optional diffusing structure 43 is placed in front of the illuminator panel 45 to diffuse light and generate more uniform light output. The diffusing structure 43 could include one layer or a plurality of sublayers of diffusers.

A polarizer structure 2 is placed in front of the optional diffusing layer 43. There are many possible embodiments of polarizer structure 2, including but not limited to a linear polarizer, or a circular polarizer. In a preferred embodiment of this invention, a circularly polarized light illumination is chosen due to symmetry. If the circularly polarized light is used in the illumination, one embodiment of the polarizer structure 2 is a combination of a linear polarizer and an appropriately orientated quarter-wave plate. The quarter-wave plate is broadband, covering the employed spectrum, determined by the light source spectrum and the responsive spectrum of the detector system. In practice, the quarter-wave plate might not be exactly quarter-wave at all the spectral region. Any deviation of the optical path length from a quarter-wave due to fabrication limitation of the waveplate could be minimized in the calibration process that will be described hereinafter.

Note in this invention, the polarization states are all defined from the receiver (detector) point of view, against the light propagation direction.

Figure 6:
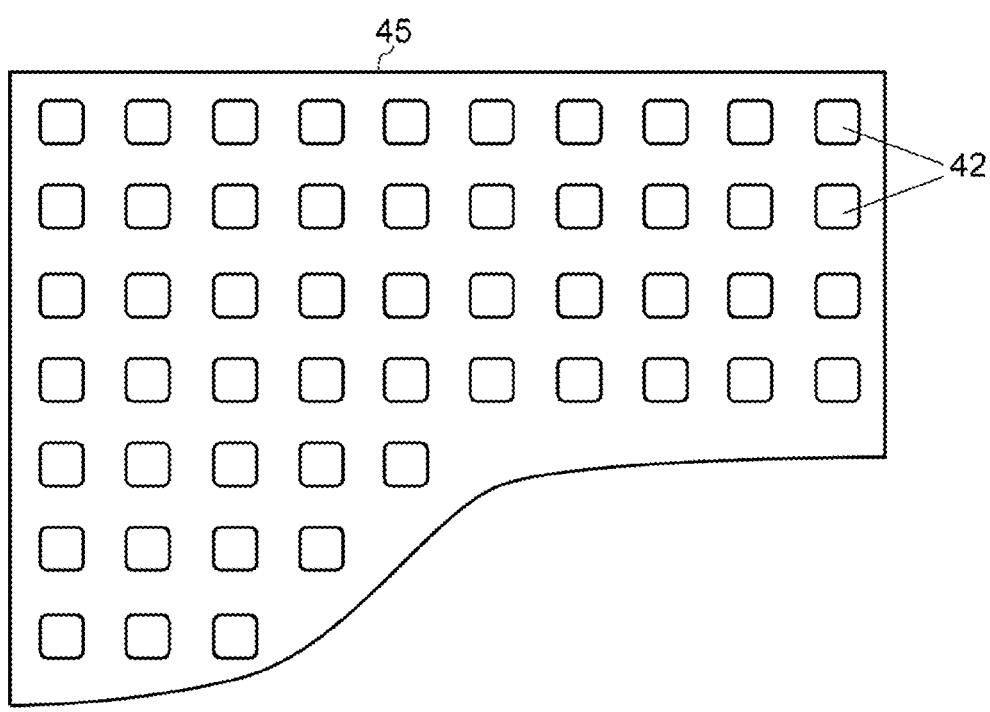
FIG. 6 illustrates the unwrapped layout of one possible arrangement array of individual light sources forming a panel as part of the illuminator.

The light source 1 comprises an illuminator panel 45, and an optional diffusing structure 43. The light source 1 in the illuminator is a broadband light source, including but not limited to a white light source. In one embodiment, the illuminator panel 45 is composed of an array of white LEDs placed on a mechanical support. Other light sources are also possible, including but not limited to incandescent light, fluorescent light, and organic light emitting diodes (OLEDs). FIG. 6 shows an unwrapped layout of one possible arrangement array of individual light sources 42 in the illuminator panel 45 without the optional covering diffusing structure 43.

The choice of the exact size of the illuminator depends on the sample under test, and preferably, the opening end of the illuminator is slightly larger than the region of interest of the sample under test to ensure enough sample coverage while blocking unwanted stray light.

In FIG. 1, after passing the polarizer structure 2, polarized light 5 is directed toward the sample 3 under test. The sample 3 could be curved. It could be either spherical or near spherical, convex or concave. It could also be cylindrical or near cylindrical, convex or concave. A freeform sample could also be tested with the system disclosed in this invention, given that the freeform sample could be decomposed into simple segments that can be approximated as a combination of several spherical, cylindrical, or flat segments, which could be individually tested. If a thin film coating on a freeform sample is to be tested, a reference phantom of the same freeform shape could be used to calibrate the sample, or multiple phantoms resembling different segments of the freeform sample could be used as reference phantoms to calibrate these segments individually.

In FIG. 1, the system has an optical axis 4. The reflected light 6 passes through an imaging group 18. The possible embodiment of imaging group 18 includes but is not limited to a lens group, a reflective imaging system, a diffractive imaging group, or a catadioptric optical system. The design of the imaging group 18 has to be balanced with the rest of the optical system in the optical path to minimize aberration on the detector plane. In FIG. 1, a two-doublet lens system is used for illustration purposes. In this design, reflected light 6 passes through an aperture stop 7, and then passes through two achromatic doublets 8 and 9. The ray path in FIG. 1 presents the chief ray of one off-axis field point.

In FIG. 1, light 10 after the imaging group 18 hits a beamsplitter 11. The beamsplitter is a non-polarizing beamsplitter so that the two output polarization states of the beamsplitter remain substantially the same as the input polarization state. There are many possible embodiments of the non-polarizing beamsplitter, including but not limited to a cube beamsplitter, a plate beamsplitter, a pellicle beamsplitter, and a diffractive beamsplitter. These embodiments of beamsplitters are not limited to the two-detector system, but also apply to the system with more detectors as described hereinafter.

Preferably, the beamsplitter in a two-detector system has a splitting ratio of 50:50. If the splitting ratio is not 50:50, beamsplitter compensating factors have to be taken into account in the calibration and analysis procedure. If the beamsplitter is not perfectly non-polarizing, the polarizing effect due to the discrepancy of the transmission and reflection of light of p polarization (p pol) and s polarization (s pol) can be minimized in the calibration process to be described hereinafter.

In FIG. 1, after the beamsplitter, light 10 breaks up into two optical branches, one branch of light 12 passes through a polarization analyzer 15 and reaches a detector 17, and the other branch of light 13 passes through a polarization analyzer 14 and reaches a detector 16. Preferably, the two analyzers are orthogonal polarizers. In a preferred embodiment, one of the analyzer is a circular polarizer, the transmission polarization of the circular polarizer is the same as the polarization of the illumination light, and the transmission polarization of the other analyzer is orthogonal to the polarization of the illumination light.

Detectors 16 and 17 are optionally connected to a processor or a computer to be further analyzed. In a preferred embodiment, real time images are displayed to facilitate alignment and measurement monitoring. Preferably, pairs of images captured by these two detectors are substantially synchronized, which is helpful to minimize registration errors for dynamically evolving or moving thin film coating analysis. Preferably, the capturing time difference, or the synchronization error, for each pair of images of the two detectors is less than the elapsed time for the dynamic thin film coating image series on the detectors to change by one pixel. For tear film lipid layer measurement, the capturing time difference is preferably less than 0.2 seconds.

Figure 2:
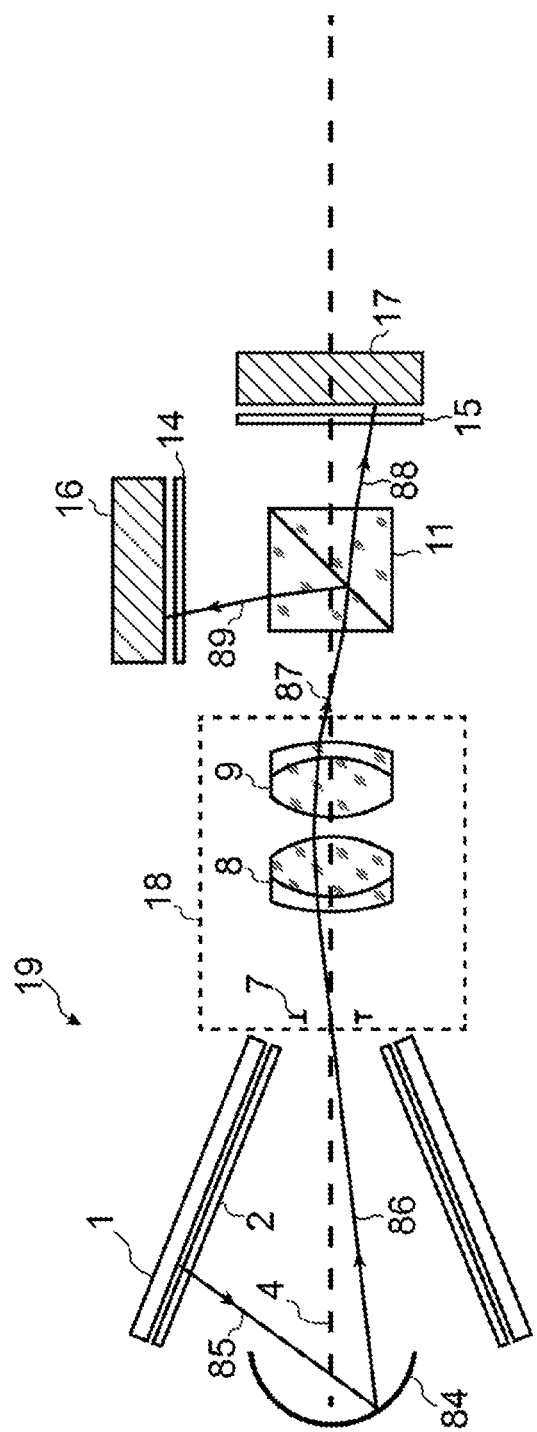
FIG. 2 illustrates the same apparatus embodiment as in FIG. 1, but applies to the measurement of a concave surface.

FIG. 2 illustrates the same thin film analysis apparatus 19 as in FIG. 1, but with a different sample 84. The sample 84 has a concavely curved surface, instead of a convexly curved surface in the sample 3 as shown in FIG. 1. Similar to the embodiment in FIG. 1, polarized illumination light 85 from light source 1 and polarizer structure 2, is reflected from the sample 84, and reflected light 86 passes the imaging group 18 and output light 87 is split into two channels, light 88 and 89, which reach detector 17 and 16 respectively, after passing corresponding analyzers 15 and 14.

Figure 3:
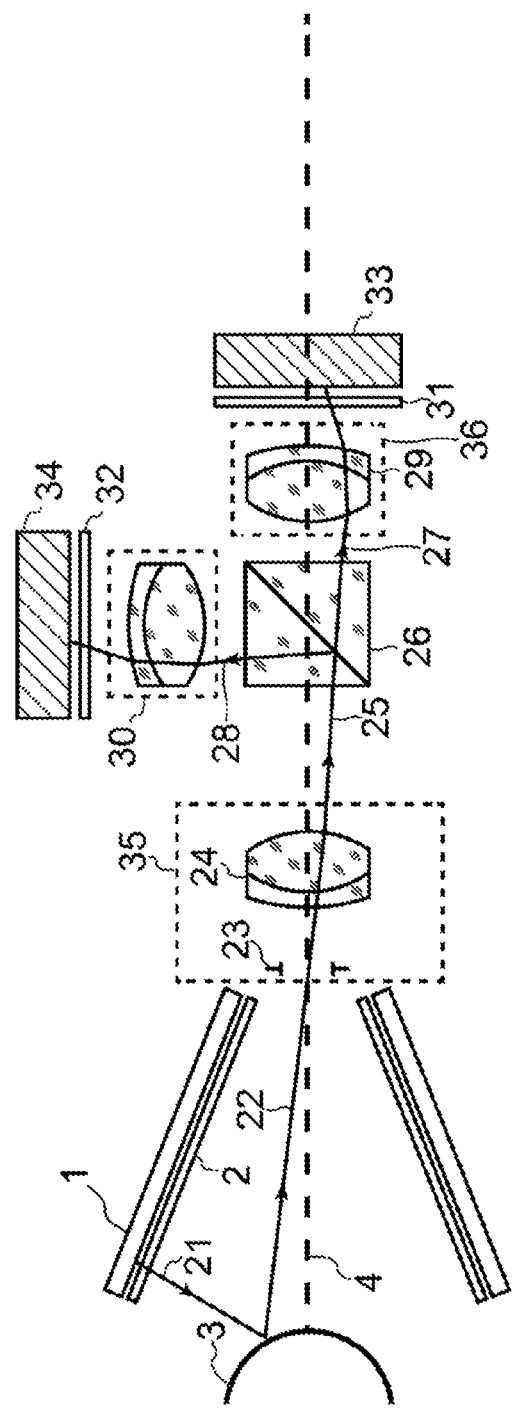
FIG. 3 is another preferred embodiment of a two-detector system.

FIG. 3 illustrates another preferred embodiment of a two-detector system of this invention. The main difference in FIG. 3, compared with FIG. 1, is that after the imaging group and the beamsplitter, there is a focusing group in each optical branch to collect the light onto the detector. The illumination system is the same as that of FIG. 1, a light source 1, including an optional diffusing structure 43, generates light, which passes through a polarizer structure 2. Illumination light 21 is reflected from a sample 3 and reflected light 22 carries the information of the thin film coated samples or a bare substrate sample. The reflected light 22 passes through an imaging group 35 and exits as light 25. There are many possible embodiments of the imaging group 35, including but not limited to that shown in FIG. 3, which includes an aperture stop 23, and an achromatic doublet lens 24. The ray path in FIG. 3 presents the chief ray of one off-axis field point. Light 25 reaches a beamsplitter 26, and splits into two optical branches 27 and 28. Light 27 passes through a focusing group 36. The focusing group 36 could have a plurality of embodiments, including but not limited to an achromatic doublet 29, as shown in FIG. 3. The focused beam then passes through a polarization analyzer 31 and reaches a detector 33. Similarly, light 28 passes through a focusing group 30 and hits another polarization analyzer 32, and reaches a detector 34.

Similar to FIG. 1, in one preferred embodiment of FIG. 3, one of the analyzers has the same polarization orientation as that of the illumination light, and the other polarizer has a polarization orthogonal to that of the illumination light.

Figure 7:
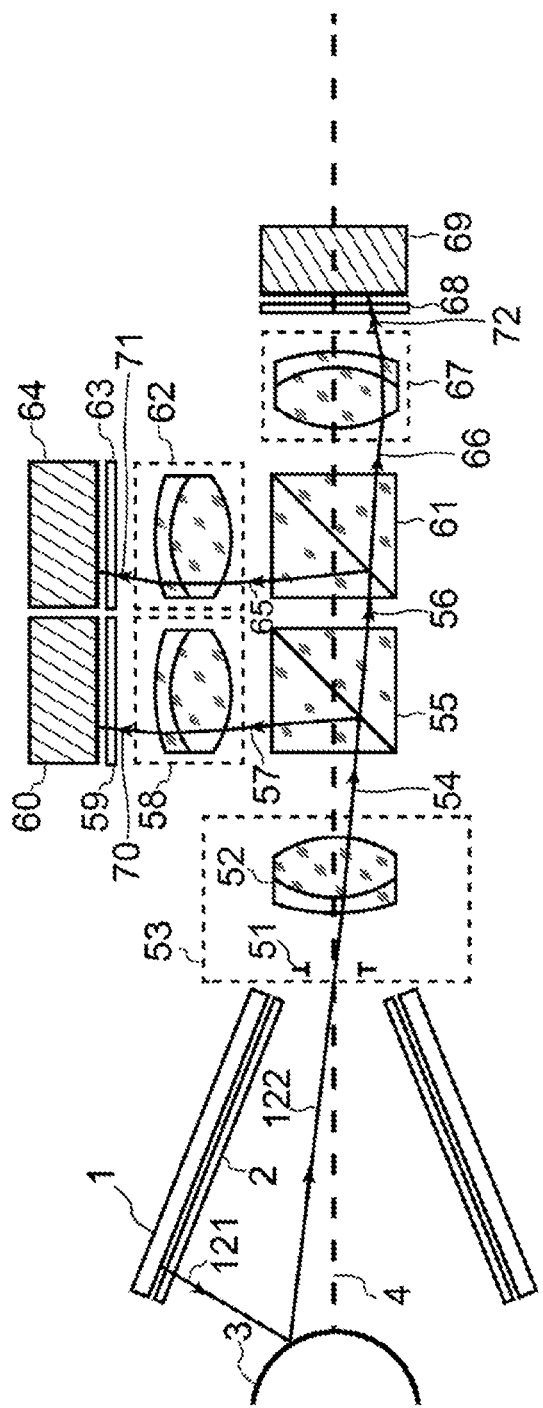
FIG. 7 presents one preferred embodiment of a three-detector system.

FIG. 7 illustrates one embodiment of the three-detector system of this invention. The illumination system has the same structure as shown in FIG. 1. Illumination light 121 from a light source 1, including an optional diffusing layer 43, passes through a polarizer structure 2 and is reflected from a sample 3. Reflected light 122 goes through an imaging group 53. One possible embodiment of the imaging group 53 is shown in FIG. 7 as an aperture stop 51 and an achromatic doublet lens 52. Light 54 reaches a first non-polarizing beamsplitter 55 and splits into two optical branches 56 and 57. Light 57 passes through a focusing group 58, and one possible embodiment of the focusing group 58 is an achromatic doublet lens as shown in FIG. 7. After passing 58, light 70 passes through a polarization analyzer 59 and reaches a detector 60. On the other hand, after passing the first beamsplitter 55, light 56 hits a second non-polarizing beamsplitter 61 and it further splits into two optical branches 65 and 66. Light 65 passes through a focusing group 62, and one possible embodiment of the focusing group 62 is an achromatic doublet lens as shown in FIG. 7. Focused light 71 passes through a polarization analyzer 63, and reaches a detector 64. Similarly, the other branch of light 66 passes through a focusing group 67 and focused light 72 passes through a polarization analyzer 68 and reaches a detector 69. In a preferred embodiment, real time images are displayed to help facilitate alignment and measurement monitoring. The recorded images or image series on detectors are optionally connected to a processor or a computer to be further analyzed.

Figure 8:
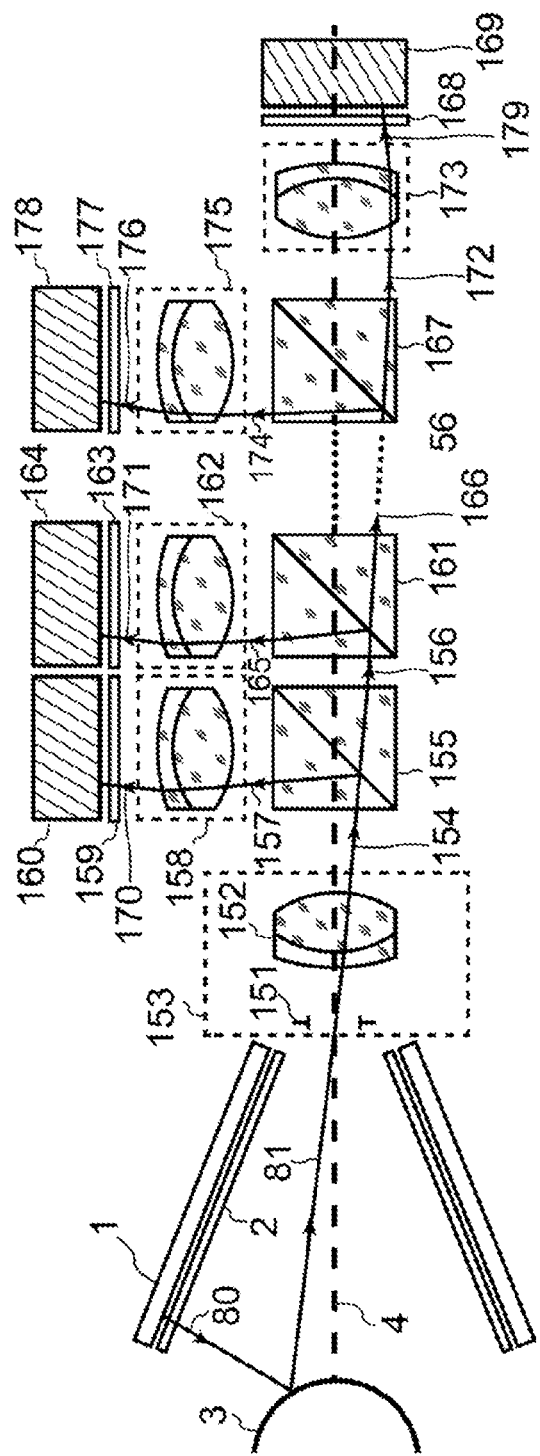
FIG. 8 is a schematic illustration of a preferred embodiment of a multiple-detector system.

FIG. 8 is a schematic illustration of a multiple-detector system of this invention. The illuminator has the same structure as shown in FIG. 1. Illumination light 80 from a light source 1, including an optional diffusing layer 43, passes through a polarizer structure 2, and is reflected from a sample 3. Reflected light 81 passes through an imaging group 153. One possible embodiment of the imaging group 153 is shown in FIG. 8 as an aperture stop 151 and an achromatic doublet lens 152. Light 154 reaches a first non-polarizing beamsplitter 155, and splits into two optical branches, 156 and 157. Light 157 passes through a focusing group 158, and one possible embodiment of the focusing group 158 is an achromatic doublet lens as shown in FIG. 8. After passing 158, light 170 passes through a polarization analyzer 159 and reaches a detector 160. In the other branch, light 156 hits a second non-polarizing beamsplitter 161 and it further splits into two optical branches 165 and 166. In a similar manner as light 157, light 165 passes through a focusing group 162, and focused light 171 passes through a polarization analyzer 163, and reaches a detector 164. Similarly, light 166 continues to split every time it reaches a non-polarizing beamsplitter, and one branch goes through a focusing group, a polarization analyzer and reaches a detector, while the other branch continues to go through the following optics. The last non-polarizing beamsplitter is a beamsplitter 167 in FIG. 8, and light splits into two optical branches 172 and 174. Light 172 passes through a focusing group 173, and output light 179 passes through a polarization analyzer 168 and reaches a detector 169. The other branch of light 174 passes through a focusing group 175 and focused light 176 passes through a polarization analyzer 177 and reaches a detector 178. All the analyzers in the system have different orientations. In a preferred embodiment, real time images are displayed to help facilitate alignment and measurement monitoring. The recorded images or image series on detectors are optionally connected to a processor or a computer to be further analyzed.

2. Theoretical Framework

In a preferred embodiment, this invention employs fully polarized light as the illumination. If the illumination light is partially polarized and there is a depolarized portion of the illumination light, the effect of the depolarized portion can be minimized with a reference phantom during the calibration process.

Without losing generality, Jones Calculus can be employed to analyze the system, with the assumption of fully polarized illumination. The more general case of partially polarized illumination will be discussed hereinafter.

Starting with the system illustrated in FIG. 1, the general form of Jones calculus for FIG. 1 is:

$$E_{ok} = A_k B_k I \Phi_2 R \Phi_1 E_i \quad (1)$$

where $E_i = [E_{ix}, E_{iy}]^T$ is the input polarization of a chief ray in a local coordinate system on a point of the illuminator. The local coordinates have a latitude and a longitude component. $\Phi_1$ is a 2×2 rotation matrix that rotates the local input field components into the p and s polarization components of the point where the chief ray intersects on the sample. On the point where the chief ray is specularly reflected off the sample, the plane of incidence is defined as the plane containing both the surface normal and the incident ray. The p polarization (p pol) and s polarization (s pol) components lie parallel and perpendicular to the plane of incidence, respectively. R is a 2×2 reflection matrix in the local p and s basis. $\Phi_2$ is a 2×2 rotation matrix that rotates the reflected electric field of the chief ray from the p and s basis of a point in the sample to another latitude and longitude basis centered on the optical axis 4 in FIG. 1. I is a 2×2 matrix characterizing the polarization of the imaging group 18, and $B_k$ is a 2×2 matrix charactering the beamsplitter, k=1 or 2 to denote the two optical branches of the beamsplitter. In an ideal setup, the beamsplitter should be perfectly non-absorptive and non-polarizing, so that $$B_1 = c_1 \begin{bmatrix} 1 & 0 \\ 0 & 1 \end{bmatrix}, B_2 = c_2 \begin{bmatrix} 1 & 0 \\ 0 & 1 \end{bmatrix},$$

where $c_1^2 + c_2^2 = 1$, and the radiance splitting ratio is $c_1^2 : c_2^2$. For the specific case of 50:50 equal splitting ratio, $$B_1 = B_2 = B = \frac{\sqrt{2}}{2} \begin{bmatrix} 1 & 0 \\ 0 & 1 \end{bmatrix}.$$

If there is residual polarizing effect of the non-polarizing beamsplitter, $$B_1 \neq \frac{c_1}{c_2} B_2, \text{ but } B_1 \approx \frac{c_1}{c_2} B_2.$$

Experimentally, a small amount of light will be absorbed by the beamsplitter, and these beamsplitters almost always have some residual polarizing effect, and this residual polarizing effect can be minimized by the reference phantom during the calibration process as described below. $A_k$ is a 2×2 polarization analyzer matrix. In a preferred embodiment, $A_1$ and $A_2$ have orthogonal polarization states, and one has the same polarization as that of the illumination light, and the other has the orthogonal polarization of the illumination light. $E_{ok} = [E_{okx}, E_{oky}]^T$ is the output electric field in optical branch k.

During the measurement, the reflected images of the sample are taken, and if the sample is dynamically evolving, a series of images are captured for analysis.

A reference phantom is also measured with the same setup, and the reference phantom has a robust, known optical structure. Preferably, the reflectance off the sample, and the reflectance off the reference phantom should be close, so that a high dynamic range detector is not necessarily required. In general, high reflectance samples should be matched with high reflectance reference phantoms, such as curved phantoms made of high refractive index glasses or even metal, while low reflectance samples should be matched with low reflectance reference phantoms, such as those made of glasses with low refractive index, or anti-reflection coated glass substrates, etc.

For a plurality of testing purposes, such as the human tear film lipid layer measurement, a bare substrate BK7 glass with the same or substantially similar radius of curvature as the sample, such as the human cornea, would suffice as a reference phantom.

With the calibration process of a reference phantom, the matrices I, $\Phi_1$, and $\Phi_2$ can be dropped, and the beamsplitter can be modeled as an ideal non-polarizing beamsplitter $$B_1 = c_1 \begin{bmatrix} 1 & 0 \\ 0 & 1 \end{bmatrix}, B_2 = c_2 \begin{bmatrix} 1 & 0 \\ 0 & 1 \end{bmatrix},$$

where $c_1^2 + c_2^2 = 1$.

Therefore, the analysis procedure can be simplified as $$E_{ok} = A_k B_k R E_i \quad (2)$$

The reason is explained as follows. To model the beamsplitter as an ideal non-polarizing beamsplitter, the weak absorption and residual polarizing effect of the beamsplitter are ignored. This is justified because the weak absorption and polarizing effects of the non-polarizing beamsplitter are minimized during the calibration with a reference phantom, since the reflected light from the reference phantom will experience proportionally the same amount of weak absorption and polarizing effect.

Similarly, the imaging group matrix I can be dropped, because the reflected light off the sample and the reference phantom will experience proportionally the same polarization change caused by the imaging group, such as the imaging lenses.

As for the rotation matrices $\Phi_1$ and $\Phi_2$, due to the same or similar geometrical setup of the sample and the reference phantom, there will be the same or similar rotational coordinates transform for both the sample and the reference phantom sample. These rotation matrices can be dropped, and the calibration process can be used to minimize the resultant errors.

For another two-detector system shown in FIG. 3, the general form of Jones calculus is $$E_{ok} = A_k F_k B_k I \Phi_2 R \Phi_1 E_i \quad (3)$$

where $F_k$ is a 2×2 matrix charactering the polarization of the focusing group 30 or 36. In a similar manner, the focusing group matrix $F_k$ can be dropped, because in both branches after the beamsplitter, the reflected light off the sample and the reference phantom will experience proportionally the same polarization change caused by the focusing group. The rest part of the formula denotes the same parts as in FIG. 1. Therefore, the analysis procedure can be simplified as Equation (2) as well.

With the above consideration of these two different types of two-detector systems, the simplified Jones calculus form is used in the following, and for a fully polarized incident beam $$E_i = \begin{bmatrix} a \\ b e^{i\delta} \end{bmatrix} \quad (4)$$

where $a^2 + b^2 = 1$. The coefficients a and b are the amplitude of p pol component and s pol component, respectively, and they both are non-negative real numbers.

The reflection matrix of the sample is $$R = \begin{bmatrix} r_p e^{i\delta_p} & 0 \\ 0 & r_s e^{i\delta_s} \end{bmatrix} \quad (5)$$

where $r_p$ and $r_s$ are the amplitude reflectivity of the electric field for p and s polarization respectively.

The reflection matrix of the reference phantom is $$R_0 = \begin{bmatrix} r_{p0} e^{i\delta_{p0}} & 0 \\ 0 & r_{s0} e^{i\delta_{s0}} \end{bmatrix} \quad (6)$$

The resultant electric field after reflection off the sample is $$RE_i = \begin{bmatrix} a r_p e^{i\delta_p} \\ b r_s e^{i(\delta_s + \delta)} \end{bmatrix} = e^{i\delta_s} \begin{bmatrix} a r_p e^{i\Delta} \\ b r_s e^{i\delta} \end{bmatrix} \quad (7)$$

where $\Delta = \delta_p - \delta_s$. The constant phase factor $e^{i\delta_s}$ will be dropped, since only the irradiance values will be analyzed in the following.

Similarly, the electric field after reflection off the reference phantom is $$R_0 E_i = \begin{bmatrix} a r_{p0} e^{i\delta_{p0}} \\ b r_{s0} e^{i(\delta_{s0} + \delta)} \end{bmatrix} = e^{i\delta_{s0}} \begin{bmatrix} a r_{p0} e^{i\Delta_0} \\ b r_{s0} e^{i\delta} \end{bmatrix} \quad (8)$$

where $\Delta_0 = \delta_{p0} - \delta_{s0}$, and similarly, the constant phase factor $e^{i\delta_{s0}}$ so can be dropped.

For example, if the illumination is of left-hand circular polarization, the input electric field is $$E_i = \frac{\sqrt{2}}{2} \begin{bmatrix} 1 \\ i \end{bmatrix} \quad (9)$$

After reflection off the sample, the electric field is $$RE_i = \frac{\sqrt{2}}{2} \begin{bmatrix} r_p e^{i\Delta} \\ i r_s \end{bmatrix} \quad (10)$$

If the first analyzer is a right-hand circular (RHC) polarizer, its polarization matrix is $$A_1 = \frac{1}{2}\begin{bmatrix} 1 & i \\ -i & 1 \end{bmatrix}, \quad (11)$$

If the beamsplitter is a 50:50 equally splitting, non-polarizing beamsplitter, the output electric field is $$E_{o1} = A_1 BRE_i = \frac{1}{4}\begin{bmatrix} r_p e^{i\Delta} - r_s \\ -ir_p e^{i\Delta} + ir_s \end{bmatrix}. \quad (12)$$

If the second analyzer is a left-hand circular (LHC) polarizer, orthogonal to the first analyzer, the second analyzer matrix is $$A_2 = \frac{1}{2}\begin{bmatrix} 1 & -i \\ i & 1 \end{bmatrix}, \quad (13)$$

and the output electric field is $$E_{o2} = A_2 BRE_i = \frac{1}{4}\begin{bmatrix} r_p e^{i\Delta} + r_s \\ ir_p e^{i\Delta} + ir_s \end{bmatrix}. \quad (14)$$

Since a normalized electric field as the input was assumed at the beginning, the "absolute effective reflectance" of the irradiance could be defined as $$AER_1 = |E_{o1}|^2 = \frac{1}{8}(r_p^2 - 2r_p r_s \cos\Delta + r_s^2) \quad (15)$$

The name "absolute effective reflectance" (AER) refers to the fact that it represents a ratio, the irradiance of the portion of the reflected light that can pass through an analyzer, divided by the irradiance of the fully polarized illumination light. Hence, the irradiance of the output electric field after an analyzer is proportional to the absolute effective reflectance.

The absolute effective reflectance of the output electric field after the second analyzer is $$AER_2 = |E_{o2}|^2 = \frac{1}{8}(r_p^2 + 2r_p r_s \cos\Delta + r_s^2) \quad (16)$$

If only the relative reflectance values are of concern, the constant factor "⅛" in the absolute effective reflectance can be further dropped to obtain simpler mathematical forms. The effective reflectance after the first analyzer is defined as $$ER_1 = r_p^2 - 2r_p r_s \cos\Delta + r_s^2. \quad (17)$$

The effective reflectance after the second analyzer is $$ER_2 = r_p^2 - 2r_p r_s \cos\Delta + r_s^2. \quad (18)$$

If the splitting ratio of the beamsplitter is not 50:50, the beamsplitter compensating factors have to be taken into account in the effective reflectance to compensate for the unequal distribution of power in the two optical branches of the beamsplitter.

Similarly, the effective reflectance values for a reference phantom can be derived as $$ER_{01} = r_{p0}^2 - 2r_{p0} r_{s0} \cos\Delta_0 + r_{s0}^2 \quad (19)$$

and $$ER_{01} = r_{p0}^2 - 2r_{p0} r_{s0} \cos\Delta_0 + r_{s0}^2 \quad (20)$$

The irradiance of the output electric field is proportional to the effective reflectance ER. The data number at each individual detector pixel is also proportional to the effective reflectance ER. This proportionality is valid, except in the cases of extremely strong or weak illumination. In the strong illumination case, the pixels on the detectors could be saturated, and thus lose the linearity. In the case of low light conditions, the reflected light signal could be so weak that the signal is buried in a noisy background, and lose the proportionality of the data number to the input light signal.

With properly chosen illumination, exposure time, and reference phantom, these extreme cases could be avoided and the proportionality is valid. The two effective reflectance values of the sample can be written as $$\frac{DN_1}{m_1} = r_p^2 - 2r_p r_s \cos\Delta + r_s^2 \text{ and} \quad (21)$$

$$\frac{DN_2}{m_2} = r_p^2 + 2r_p r_s \cos\Delta + r_s^2 \quad (22)$$

where DN stands for the data number at each pixel of each color channel, $DN_1$ and $DN_2$ are for the two detectors of the two optical branches. $m_1$ and $m_2$ are two scaling factors, and these two scaling factors can be experimentally calibrated by a reference phantom.

If the sample under test is replaced with a reference phantom of the same or substantially similar shape as the sample, the above two equations still hold. The reference phantom has known optical structures, so that the reflection coefficients $r_{p0}$, $r_{s0}$ and $\Delta_0$ are all known.

For a plurality of applications, a bare BK7 substrate with a proper radius of curvature could be used as a reference phantom. For example, in the case of the human tear film lipid layer measurement, a bare BK7 spherical substrate with a radius of curvature of 7.8 mm could be used as a reference. The radius of 7.8 mm is chosen because it is close to the average of the anterior corneal radius of human eyes. Even though there is individual variation of the anterior corneal radius from person to person, and precisely speaking, the cornea shape is not a perfect spherical surface, but rather a freeform shape with some deviation from a spherical surface, yet the anterior corneal radius will still be close to a spherical surface. A reference phantom with 7.8 mm radius is substantially close to the sample under test, which is the human cornea in this specific example.

The two effective reflectance values of the reference phantoms are $$\frac{DN_{01}}{m_1} = r_{p0}^2 - 2r_{p0} r_{s0} \cos\Delta_0 + r_{s0}^2 \text{ and} \quad (23)$$

$$\frac{DN_{02}}{m_2} = r_{p0}^2 + 2r_{p0} r_{s0} \cos\Delta_0 + r_{s0}^2, \quad (24)$$

Since the reflectivity coefficients $r_{p0}$, $r_{s0}$, and the relative phase shift $\Delta_0$ are all known parameters for the reference phantom, with experimentally measured data numbers at the corresponding pixels at the two detectors, the scaling factors can be calculated:

$$m_1 = \frac{DN_{01}}{r_{p0}^2 - 2r_{p0}r_{s0}\cos\Delta_0 + r_{s0}^2} \text{ and} \quad (25)$$

$$m_2 = \frac{DN_{02}}{r_{p0}^2 + 2r_{p0}r_{s0}\cos\Delta_0 + r_{s0}^2} \quad (26)$$

With the scaling factors $m_1$ and $m_2$ calculated for each pixel, and $DN_1$ and $DN_2$ measured experimentally, the effective reflectance $ER_1$ and $ER_2$ are now determined based on Equations (21) and (22).

Note that the above calculation is valid for each color channel of the detector. Usually, though not necessarily, a color detector has three color channels, red (R), green (G) and blue (B). Since both effective reflectance values $ER_1$ and $ER_2$ are determined for each color channel, in total, six effective reflectance values are determined with the aforementioned algorithm.

With $ER_1$ and $ER_2$ two independent measurements, up to two optical parameters of the thin film coating are now retrievable for each color channel. In each color channel, even though the effective reflectance ER has $r_p$, $r_s$, and $\Delta$ three unknowns, these three unknowns are not completely independent. These three parameters are determined by the thickness and refractive index of the thin film coating layer.

For example, for a Type 1 sample, where the back reflection from the structures beneath the thin film could be ignored and only the front surface is of concern, both the thickness and refractive index of the thin film could be retrieved, if the thin film coating is a single layer. If the Type 1 sample has multiple layer thin film coatings, two other types of optical parameters, such as two different coating layer thicknesses could be retrieved, if the refractive indices of all the layers and the thicknesses of the other layers are known.

Mathematically, for a single layer thin film coating with unknown thickness d and unknown refractive index n, but with an optically thick substrate with known refractive index $n_s$, appropriate search ranges of the thickness range and the refractive index range could be selected, and a lookup table of the effective reflectance pairs ($ER_1$, $ER_2$) can be created for all possible combinations of the thickness and refractive index pairs (n, d). These effective reflectance pairs in the lookup table will be compared with the effective reflectance pair measured at each pixel pair on the two detectors, thickness and refractive index (n, d) can be determined by choosing the effective reflectance pair from the lookup table that has the smallest total discrepancy with the measured ER values.

Figure 10:
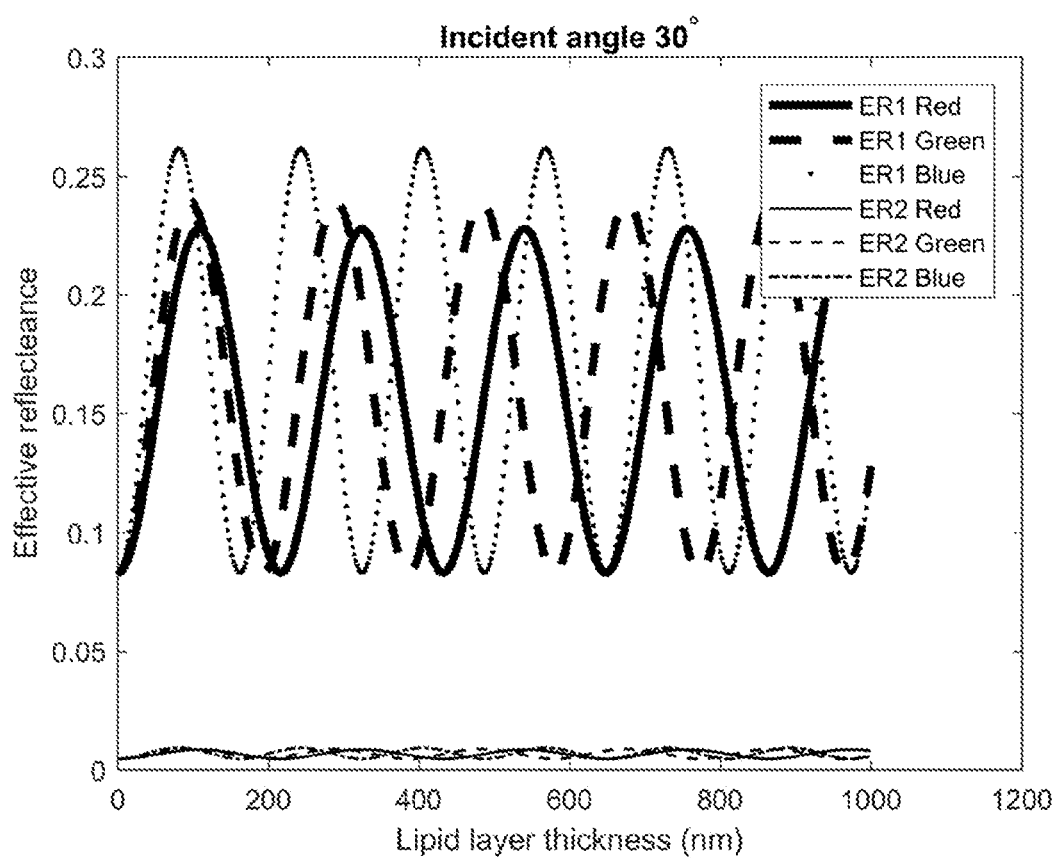
FIG. 10 is a representative effective reflectance plot of a two-detector system for the air-lipid layer-aqueous layer three-layer structure of the tear film in the human eye.

FIG. 10 is a representative effective reflectance plot of a two-detector system for the air-lipid layer-aqueous layer three-layer structure of the tear film in the human eye. It illustrates the lipid layer thickness dependence of the effective reflectance. The figure sets the incident angle of 30° as an example, and it assumes the light from the illuminator is left-hand circularly polarized, and detector 1 analyzer has right-hand circular polarization, and detector 2 analyzer has left-hand circular polarization. The average wavelengths on the detectors are modeled as red 600 nm, green 540 nm and blue 460 nm.

Figure 11:
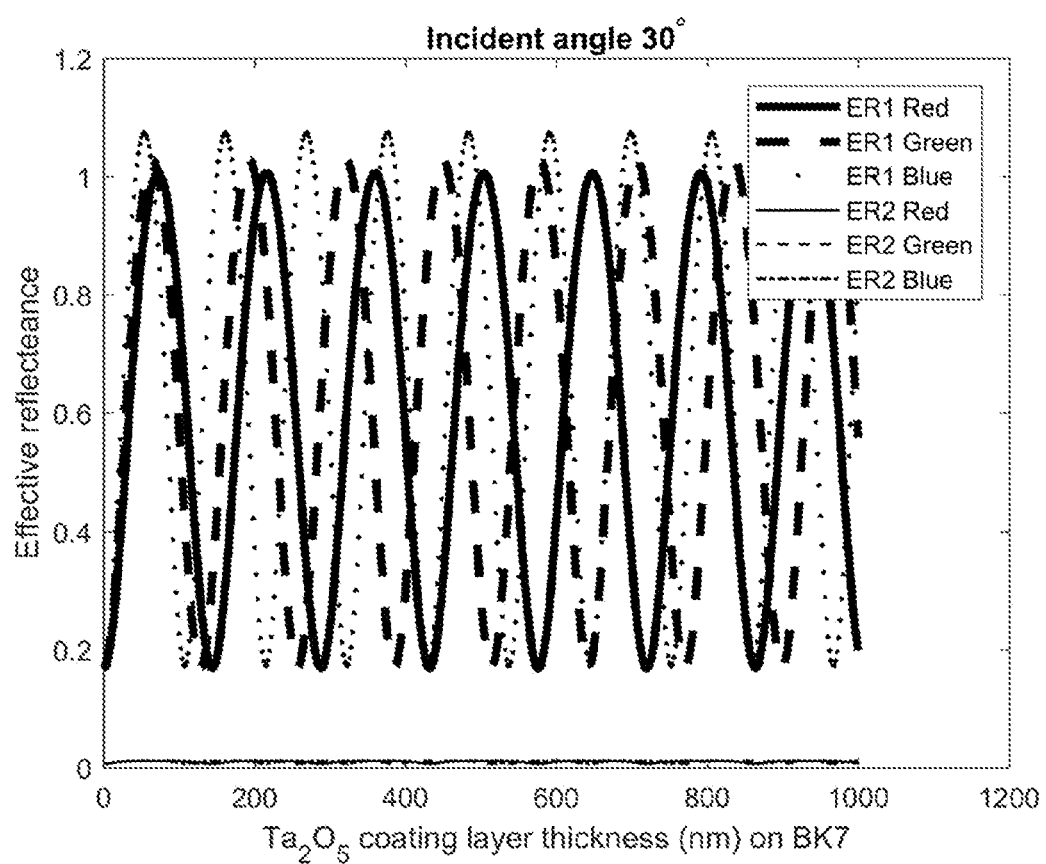
FIG. 11 is a representative effective reflectance plot of a two-detector system for a BK7 substrate coated with $Ta_2O_5$.

FIG. 11 is a representative effective reflectance plot of a two-detector system for a BK7 substrate coated with $Ta_2O_5$. It illustrates the $Ta_2O_5$ coating layer thickness dependence of the effective reflectance. The figure sets the incident angle of 30° as an example, and it assumes the same system parameters as in FIG. 10.

Note that the aforementioned thickness and refractive index (n, d) can be calculated at each color channel, and experimentally, the average wavelength arrived at the detector of each color channel can be used for the analysis. However, the thickness dependence of the effective reflectance is periodic, as shown in FIGS. 10 and 11. If only one color channel is used for the thickness and refractive index (n, d) retrieval, the thickness search range will have to be limited within one periodic cycle of the thickness dependence. Otherwise, ambiguity will arise, and there may be several different thickness values that would lead to the same measured effective reflectance values.

To resolve this ambiguity, two or more color channels could be used. As shown in FIGS. 10 and 11, the off-beat of different wavelengths will resolve the ambiguity of the thickness dependence and enable a unique thickness value in a much larger search range.

For a Type 2 sample, where there is a depolarizing element beneath the front surface, the scattered, depolarized light from that depolarizing element has to be taken into account, and the output irradiance values from these two detectors should be subtracted from each other to get rid of the depolarized light contribution to the signal on the detector. After the subtraction of the two effective reflectance values, only one independent optical parameter of the thin film coating could be retrieved. For example, if there is a single layer thin film coating on a substrate, the thickness of the thin film coating is retrievable, given a known refractive index of the thin film, or the refractive index of the thin film is retrievable, given a known thickness of the thin film. In the special case of a bare substrate, the refractive index of an unknown substrate is retrievable using this method.

Mathematically, for a Type 2 sample, the data number DN of a pixel on the detector is proportional to the sum of the effective reflectance and the scattered depolarized light $$\frac{DN_1}{m_1} = ER_1 + S \text{ and} \quad (27)$$

$$\frac{DN_2}{m_2} = ER_2 + S \quad (28)$$

The scattered light contribution S is the same for both detectors under the assumption that the depolarizing process of the depolarizing scatter beneath the front surface is sufficient, such that the output from that depolarizing element is approximately fully unpolarized.

Subtracting the two detector images, yields $$\frac{DN_2 - DN_1}{m_{21}} = ER_2 - ER_1 \quad (29)$$

Similarly, the same procedure can be applied to experimental data from a reference phantom, and if the data number of the corresponding pixel pairs are $DN_{01}$ and $DN_{02}$ for the reference phantom, $$\frac{DN_{02} - DN_{01}}{m_{21}} = ER_{02} - ER_{01} \quad (30)$$

The data number $DN_2$ and $DN_1$ can be experimentally measured, and the scaling factor $m_{21}$ can be calibrated from the reference phantom with known optical properties.

Apply the above general form to the previous exemplary setup, following the same illumination and analyzer polarization choices, $$\frac{DN_2 - DN_1}{m_{21}} = 4r_p r_s \cos\Delta, \text{ and} \tag{31}$$

$$\frac{DN_{02} - DN_{01}}{m_{21}} = 4r_{p0} r_{s0} \cos\Delta_0 \tag{32}$$

Similarly to the previous analysis, the three unknowns $r_p$, $r_s$, and $\Delta$ are not completely independent and they are determined by the thickness and refractive index of the thin film coating layer.

Using a Type 2 sample with a single layer thin film with known refractive indices at different color channels, but unknown thickness d as an example, following similar procedure as described above, a lookup table of the mutual subtraction values of effective reflectance pairs ($ER_2 - ER_1$) can be created for all the possible thickness values. These mutual subtraction values of effective reflectance pairs will be compared with the mutual subtraction value of the effective reflectance pair measured at each pixel pair on the two detectors, thickness d can be determined by choosing the effective reflectance pair from the lookup table that has the smallest total discrepancy with the measured $ER_2 - ER_1$ value.

Note that since two detectors are employed in the embodiment illustrated in FIG. 1, an important step in analyzing the images from the two detectors is to align the images from these two detectors to accurately locate and match the pixel pairs. Therefore, the registration process is important to retrieve the optical parameters accurately. Experimentally, three or four or even more registration light sources such as LEDs could be placed in a concentric circle with the center substantially aligned with the optical axis of the following imaging group. Further, to prevent possible obstruction of the illumination, it is preferred to locate these registration light sources at the rim of the front edge of the aperture stop of the imaging group facing the sample. The reflected images of these registration light sources could be used to align the images of the two detectors, or even more detectors, as in the three-detector or multiple-detector systems described in this invention.

More importantly, if the reference phantom is similar but not the same in geometry as the sample under test, these registration light sources could be used to resize and scale the images of the reference phantom to those of the sample, or vice versa, to match each other in the analysis procedure.

Figure 9:
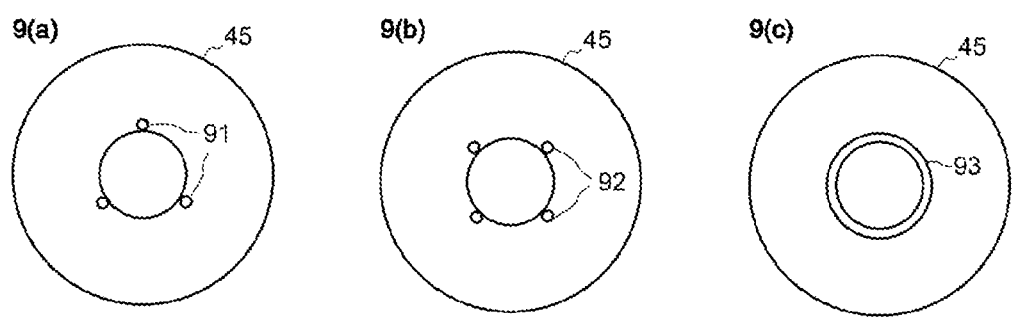
FIG. 9 illustrates three possible embodiments of the location of registration light sources.

FIG. 9 illustrates the location of the registration light sources at the anterior rim of the aperture stop of the imaging group, facing the sample. In FIG. 9(a), three registration light sources 91 are used, and in a preferred embodiment, three LEDs are used as the registration light sources. In FIG. 9(b), four registration light sources 92 are used. In FIG. 9(c), a circular-shaped registration light source 93 is used.

Furthermore, a fully polarized incident light is assumed in the above analysis. However, if the incident light is not fully polarized, but has a certain degree of polarization that is less than 1, the incident beam can be decomposed into a fully polarized part, and a fully unpolarized part. The fully polarized part will go through the aforementioned analysis procedure. The fully unpolarized part of the illumination light will have the degree of polarization increased after reflection due to the different Fresnel reflection coefficients of p-pol and s-pol. This increase in the degree of polarization is especially significant, when the incident beam is at a large incident angle close to the Brewster's angle. The Brewster's angle is dependent on the refractive index of the materials at the interface, and if the two refractive indices are $n_1$ and $n_2$, respectively, the Brewster's angle is $\arctan(n_2/n_1)$. For an air-water interface, the Brewster's angle is about 53°, and for an air-lipids interface, the Brewster's angle is about 56°, if the lipids refractive index is assumed to be about 1.48. When the angle of reflection is close to the Brewster's angle, the effective reflectance values recorded on each detector will be biased by the unpolarized part of the illumination. Even after the mutual subtraction of the effective reflectance values, the error still partially remains.

In a preferred system, the illumination system are designed such that all the incident angles are far away from the Brewster's angle. For the application of the human tear film lipid layer measurement, all the incident angles are preferably within the range of 0° to 40°, substantially far away from the Brewster's angle. Hence the increase in the degree of polarization for the unpolarized part of the illumination is limited. The process of mutual subtraction of the effective reflectance at different detectors will cancel most of the contribution from the unpolarized part of the illumination, since it remains mostly unpolarized even after the reflection for small incident angles.

More importantly, even if there are residual errors caused by the small increase in the degree of polarization of the original unpolarized part of the illumination, the calibration process with a reference phantom will further minimize the residual errors. Because there will be similar amount of increase in the degree of polarization after reflection off the sample and off the reference phantom, and these errors are mitigated in the process of calculating the scaling factors that relates the mutual subtraction of the data numbers to the mutual subtraction of the effective reflectance values.

In summary, if the illumination light is not fully polarized, the process of mutual subtraction of the effective reflectance and the calibration of the reference phantom will minimize the error caused by the increase of the degree of polarization of the unpolarized part of the original illumination light after reflection. Since mutual subtraction of the effective reflectance is employed in the process, there will be no difference for Type 1 samples and Type 2 samples. The number of retrievable optical parameters will follow our previous analysis of Type 2 samples.

Furthermore, in a preferred embodiment, a set of calibration data with statistical analysis of the aging of the illuminator and the influence of temperature and humidity change is incorporated into the analysis software. The system performance accuracy and consistency will be slightly affected by the light source aging, temperature and humidity change in the operating room, etc. If these environmental parameters vary in the place where the apparatus of this invention is used, to ensure optimal measurement accuracy, it is preferred for the operator to input the environmental parameters such as temperature and relative humidity and the measurement date into the apparatus to ensure optimal measurement accuracy.

If the environmental parameters and date are not available or couldn't be updated in the apparatus, it is preferred to have the system calibrated every day. Even more preferably, the calibration should be done immediately before or after every measurement, to minimize the possible effect of environmental factors and the illumination aging process, etc. Similar calibration procedure consideration holds for systems with more than two detectors, as described hereinafter.

Moreover, in the previously described preferred embodiments, the illumination polarizer and the two analyzers are all of circular polarization, and the symmetry of circular polarization enhances the system robustness. However, other polarization states could also be utilized in the illumination polarizer and detector analyzers. For example, if the illuminator contains a +45° linear polarizer, and the two analyzers in front of the two detectors could be −45° and +45° linear polarizers. In this specific setup, the effective reflectance values can be readily derived following a similar analysis procedure as before, and the results happen to be the same as Equations (17) and (18).

In a preferred embodiment of the three-detector system shown in FIG. 7, the electric field output on the detector 60 of the reflected branch after the first beamsplitter 55 is $$E_{o1} = A_1 F_1 B_{1R} I \Phi_2 R \Phi_1 E_i \tag{33}$$

The electric field output on the detector 64 after reflection off the second beamsplitter 61 is $$E_{o2} = A_2 F_2 B_{2R} B_{1T} I \Phi_2 R \Phi_1 E_i \tag{34}$$

The electric field output on the detector 69 after transmission through the second beamsplitter 61 is $$E_{o3} = A_3 F_3 B_{2T} B_{1T} I \Phi_2 R \Phi_1 E_i \tag{35}$$

Therefore, the general form of Jones calculus for the three-detector system in FIG. 7 can be summarized as $$E_{ok} = A_k F_k B_k I \Phi_2 R \Phi_1 E_i \tag{36}$$

where k=1, 2 or 3, and $B_k$ is a 2×2 matrix characterizing all the beamsplitters, and $B_k$ itself is the product of individual beamsplitters in the light path, and the components could be either reflection or transmission matrix, as indicated above by the subscript R or T in the beamsplitter matrix symbols. Alternatively, the three optical branches can be generated with one diffractive beamsplitter with three main diffraction orders in use, and Eq. (36) still holds. The rest of the notations carry correspondingly similar meanings as in the two-detector system.

Following similar simplification procedure, with the calibration of the reference phantom, the above electric field output could be simplified as:

$$E_{ok} = A_k B_k R E_i \tag{37}$$

In the specific case where all the beamsplitters in the system are 50:50 equal-splitting, non-polarizing beamsplitters, the above results could be further simplified as $$E_{ok} = A_k B^{nb} R E_i \tag{38}$$

where B denotes the ideal 50:50 non-polarizing beamsplitter matrix of $$B = \frac{\sqrt{2}}{2} \begin{bmatrix} 1 & 0 \\ 0 & 1 \end{bmatrix}$$

and nb denotes the number of beamsplitters in the optical path before the light reaches a detector. In the case of a three-detector system, nb is either 1 or 2.

With three independent output irradiance measurements, up to three optical parameters of the system can be obtained.

An exemplary three-detector system is analyzed herein, which uses left-hand circular polarization as the illumination, and the three analyzers are of right-hand circular polarization (RHC), left-hand circular polarization (LHC), and +45° linear polarization. These polarization states choices are exemplary and are by no means the only choices of a possible system setup.

Following the exemplary setup, the normalized input electric field is $$E_i = \frac{\sqrt{2}}{2} \begin{bmatrix} 1 \\ i \end{bmatrix} \tag{39}$$

After reflection off the sample, the electric field is $$RE_i = \frac{\sqrt{2}}{2} \begin{bmatrix} r_p e^{i\Delta} \\ ir_s \end{bmatrix} \tag{40}$$

For the specific case, where all the beamsplitters are 50:50 non-polarizing beamsplitters, the beamsplitter matrix for the reflected light after the first beamsplitter is $$B_1 = B = \frac{\sqrt{2}}{2} \begin{bmatrix} 1 & 0 \\ 0 & 1 \end{bmatrix} \tag{41}$$

The beamsplitter matrices of the reflected and transmitted light after the second beamsplitter are $$B_2 = B_3 = B^2 = \frac{1}{2} \begin{bmatrix} 1 & 0 \\ 0 & 1 \end{bmatrix} \tag{42}$$

since there are two beamsplitters in the optical path.

If the first analyzer is a right-hand circular (RHC) polarizer, the first analyzer matrix is $$A_1 = \frac{1}{2} \begin{bmatrix} 1 & i \\ -i & 1 \end{bmatrix}, \tag{43}$$

the output electric field is $$E_{o1} = A_1 B_1 R E_i = \frac{1}{4} \begin{bmatrix} r_p e^{i\Delta} - r_s \\ -i r_p e^{i\Delta} + i r_s \end{bmatrix}. \tag{44}$$

If the second analyzer is a left-hand circular (LHC) polarizer, orthogonal to the first analyzer, the second analyzer matrix is $$A_2 = \frac{1}{2} \begin{bmatrix} 1 & -i \\ i & 1 \end{bmatrix}, \tag{45}$$

the output electric field is $$E_{o2} = A_2 B_2 R E_i = \frac{\sqrt{2}}{8} \begin{bmatrix} r_p e^{i\Delta} + r_s \\ i r_p e^{i\Delta} + i r_s \end{bmatrix}. \tag{46}$$

If the third analyzer is a +45° linear polarizer, the third analyzer matrix is $$A_3 = \frac{1}{2}\begin{bmatrix} 1 & 1 \\ 1 & 1 \end{bmatrix}, \quad (47)$$

the output electric field is $$E_{o3} = A_3 B_3 R E_i = \frac{\sqrt{2}}{8}\begin{bmatrix} r_p e^{i\Delta} + ir_s \\ r_p e^{i\Delta} + ir_s \end{bmatrix}. \quad (48)$$

The absolute effective reflectance of the output electric field after the first analyzer is $$AER_1 = |E_{o1}|^2 = \frac{1}{8}(r_p^2 - 2r_p r_s \cos\Delta + r_s^2) \quad (49)$$

The absolute effective reflectance of the output electric field after the second analyzer is $$AER_2 = |E_{o2}|^2 = \frac{1}{16}(r_p^2 + 2r_p r_s \cos\Delta + r_s^2) \quad (50)$$

The absolute effective reflectance of the output electric field after the third analyzer is $$AER_3 = |E_{o3}|^2 = \frac{1}{16}(r_p^2 + 2r_p r_s \sin\Delta + r_s^2) \quad (51)$$

A beamsplitter compensating factor due to the unequal splitting ratio and/or the unequal number of beamsplitters in different optical paths can be denoted as $S_{Bk}$. For the specific case where all the beamsplitters are 50:50 beamsplitters, $S_{Bk}=2^{nb-1}$, where nb is the number of beamsplitters the light in each optical branch has passed. In the three-detector system, the second and third branches of light pass two beamsplitters, while the first branch only passes one beamsplitter, hence $S_{B1}=1$, $S_{B2}=2$, $S_{B3}=2$. Note that a constant factor can be multiplied to all the beamsplitter compensating factors without affecting the analysis results. For a diffractive beamsplitter, the beamsplitter compensating factors are determined by the diffraction efficiencies of the orders in use.

After multiplying the beamsplitter compensating factors 1:2:2 to the absolute effective reflectance values, and dropping the constant factor "⅛", the effective reflectance values are obtained:

$$ER_1 = \frac{DN_1}{m_1} = r_p^2 - 2r_p r_s \cos\Delta + r_s^2, \quad (52)$$

$$ER_2 = \frac{DN_2}{m_2} = r_p^2 + 2r_p r_s \cos\Delta + r_s^2. \quad (53)$$

$$ER_3 = \frac{DN_3}{m_3} = r_p^2 + 2r_p r_s \sin\Delta + r_s^2. \quad (54)$$

For another specific case, where the first beamsplitter has a splitting ratio of 1:2, and ⅓ goes into the reflected beam, ⅔ goes into the transmitted beam and the following optics, and the second beamsplitter has a splitting ratio of 50:50, the beamsplitter matrices of the three branches are $$B_1 = B_2 = B_3 = \frac{\sqrt{3}}{3}\begin{bmatrix} 1 & 0 \\ 0 & 1 \end{bmatrix} \quad (55)$$

Correspondingly, the output electric fields are $$E_{o1} = A_1 B_1 R E_i = \frac{\sqrt{6}}{12}\begin{bmatrix} r_p e^{i\Delta} - r_s \\ -ir_p e^{i\Delta} + ir_s \end{bmatrix}, \quad (56)$$

$$E_{o2} = A_2 B_2 R E_i = \frac{\sqrt{6}}{12}\begin{bmatrix} r_p e^{i\Delta} + r_s \\ ir_p e^{i\Delta} + ir_s \end{bmatrix}, \quad (57)$$

$$E_{o3} = A_3 B_3 R E_i = \frac{\sqrt{6}}{12}\begin{bmatrix} r_p e^{i\Delta} + ir_s \\ r_p e^{i\Delta} + ir_s \end{bmatrix}. \quad (58)$$

The absolute effective reflectance values are $$AER_1 = |E_{o1}|^2 = \frac{1}{12}(r_p^2 - 2r_p r_s \cos\Delta + r_s^2) \quad (59)$$

$$AER_2 = |E_{o2}|^2 = \frac{1}{12}(r_p^2 + 2r_p r_s \cos\Delta + r_s^2) \quad (60)$$

$$AER_3 = |E_{o3}|^2 = \frac{1}{12}(r_p^2 + 2r_p r_s \sin\Delta + r_s^2) \quad (61)$$

The beamsplitter compensating factors are $$S_{B1}=S_{B2}=S_{B3}=1 \quad (62)$$

since the total splitting ratio is 1:1:1 in this specific setup.

After multiplying the beamsplitter compensating factors 1:1:1 to the absolute effective reflectances, and dropping the constant factor "1/12", the effective reflectance values could be obtained and they have the same forms as in Equations (52)-(54).

In the two examples above with different beamsplitters choices for a three-detector system, after the multiplication of the beamsplitter compensating factors, the same effective reflectance values are obtained. The only possible difference in the effective reflectance values is a constant factor in all three detector channels, which would not affect the final optical parameter retrieval results, as long as the same constant factor is consistently used for both the sample and the reference phantom.

The multiplication of the beamsplitter compensating factors due to the unequal splitting ratio and the unequal numbers of beamsplitters in different optical paths is not absolutely necessary for Type 1 samples with fully polarized illumination light, as long as the same procedure is followed in the calibration process with the reference phantom, consistency could be achieved. Type 2 samples, however, require mutual subtraction of the light from different optical branches to get rid of the effect of the depolarizing element underneath the front surface. Therefore, the beamsplitter compensating factors have to be taken into account for Type 2 samples. Illuminators of partial polarization also require mutual subtraction of the light from different optical branches regardless of Type 1 or Type 2 samples, and hence the beamsplitter compensating factors have to be taken into account.

Similarly, the effective reflectance values for a reference phantom can be derived as $$ER_{01} = \frac{DN_{01}}{m_1} = r_{p0}^2 - 2r_{p0}r_{s0}\cos\Delta_0 + r_{s0}^2, \tag{63}$$

$$ER_{02} = \frac{DN_{02}}{m_2} = r_{p0}^2 + 2r_{p0}r_{s0}\cos\Delta_0 + r_{s0}^2, \tag{64}$$

$$ER_{03} = \frac{DN_{03}}{m_3} = r_{p0}^2 + 2r_{p0}r_{s0}\sin\Delta_0 + r_{s0}^2. \tag{65}$$

Since the reflectivity coefficients $r_{p0}$, $r_{s0}$, and the relative phase shift $\Delta_0$ are all known parameters of the reference phantom, with experimentally measured data numbers at the corresponding pixels at the three detectors, the scaling factors can be calculated:

$$m_1 = \frac{DN_{01}}{r_{p0}^2 - 2r_{p0}r_{s0}\cos\Delta_0 + r_{s0}^2}, \tag{66}$$

$$m_2 = \frac{DN_{02}}{r_{p0}^2 + 2r_{p0}r_{s0}\cos\Delta_0 + r_{s0}^2}, \tag{67}$$

$$m_3 = \frac{DN_{03}}{r_{p0}^2 + 2r_{p0}r_{s0}\sin\Delta_0 + r_{s0}^2}, \tag{68}$$

With the scaling factors $m_1$, $m_2$ and $m_3$ calculated for each pixel, and $DN_1$, $DN_2$ and $DN_3$ measured experimentally. The effective reflectances $ER_1$, $ER_2$ and $ER_3$ are now determined.

Note that the above calculation is valid for each color channel of the detector. Since effective reflectance $ER_1$, $ER_2$ and $ER_3$ are all determined for each color channel, in total, nine effective reflectance values are determined with the aforementioned algorithm for a common three-color-channel detector.

With $ER_1$, $ER_2$ and $ER_3$ three independent measurements, up to three optical parameters of the thin film coating are now retrievable for each color channel. For example, for a Type 1 sample with a single layer thin film coating with unknown thickness d and unknown refractive index n, but with an optically thick substrate with known refractive index $n_s$. Appropriate search ranges of the thickness range and the refractive index range could be selected, and a lookup table of the effective reflectance sets ($ER_1$, $ER_2$, $ER_3$) can be created for all possible combinations of the thickness and refractive index pairs (n, d). These effective reflectance sets will be compared with the effective reflectance set measured at each pixel set on the three detectors, thickness and refractive index (n, d) can be determined by choosing the effective reflectance set from the lookup table that has the smallest total discrepancy with the measured ER values.

Similarly, if the substrate index is also unknown, a lookup table of ($ER_1$, $ER_2$, $ER_3$) can be created for all possible combinations of (n, d, $n_s$) within a certain search range for each of these three unknowns.

Figure 12:
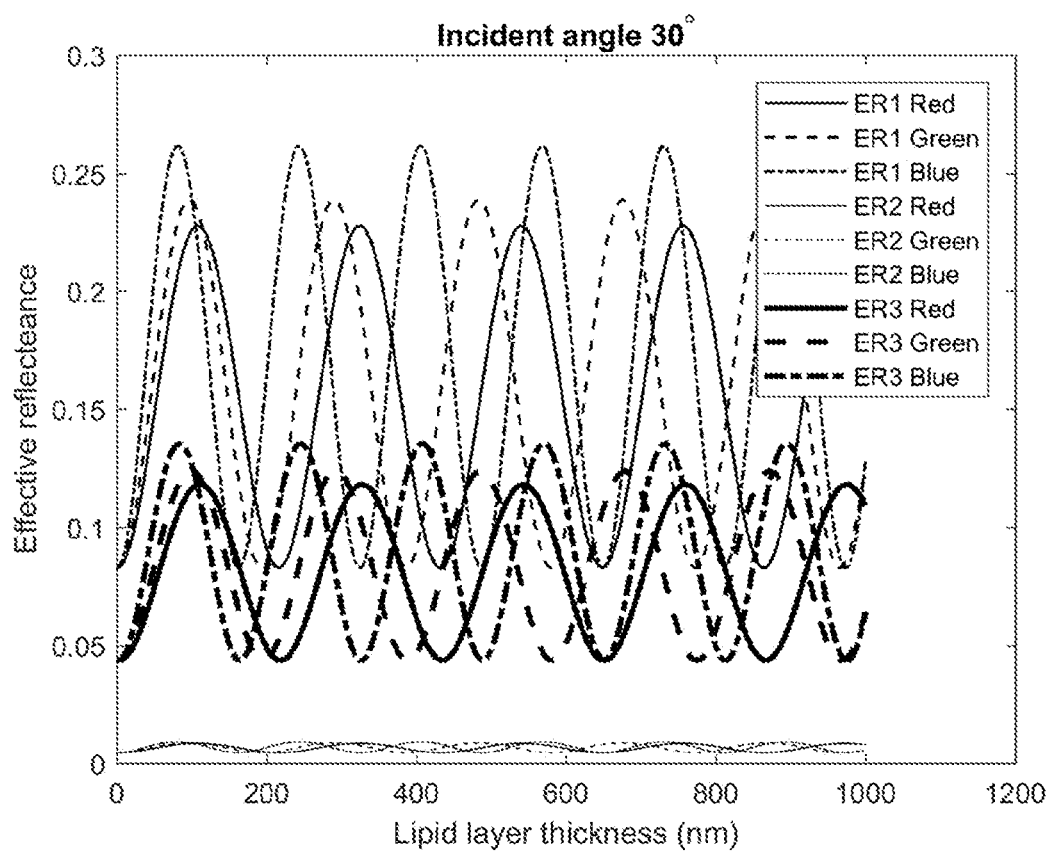
FIG. 12 is a representative effective reflectance plot of a three-detector system for the air-lipid layer-aqueous layer three-layer structure of the tear film in the human eye.

FIG. 12 is an effective reflectance plot of a three-detector system for the air-lipid layer-aqueous layer three-layer structure of the tear film in the human eye. It illustrates the lipid layer thickness dependence of the effective reflectance. The figure sets the incident angle of 30° as an example, and it assumes the light from the illuminator is left-hand circularly polarized, and detector 1 analyzer has right-hand circular polarization, detector 2 analyzer has left-hand circular polarization, detector 3 has +45° linear polarization. The average wavelengths on the detectors are modeled as red 600 nm, green 540 nm and blue 460 nm.

Figure 13:
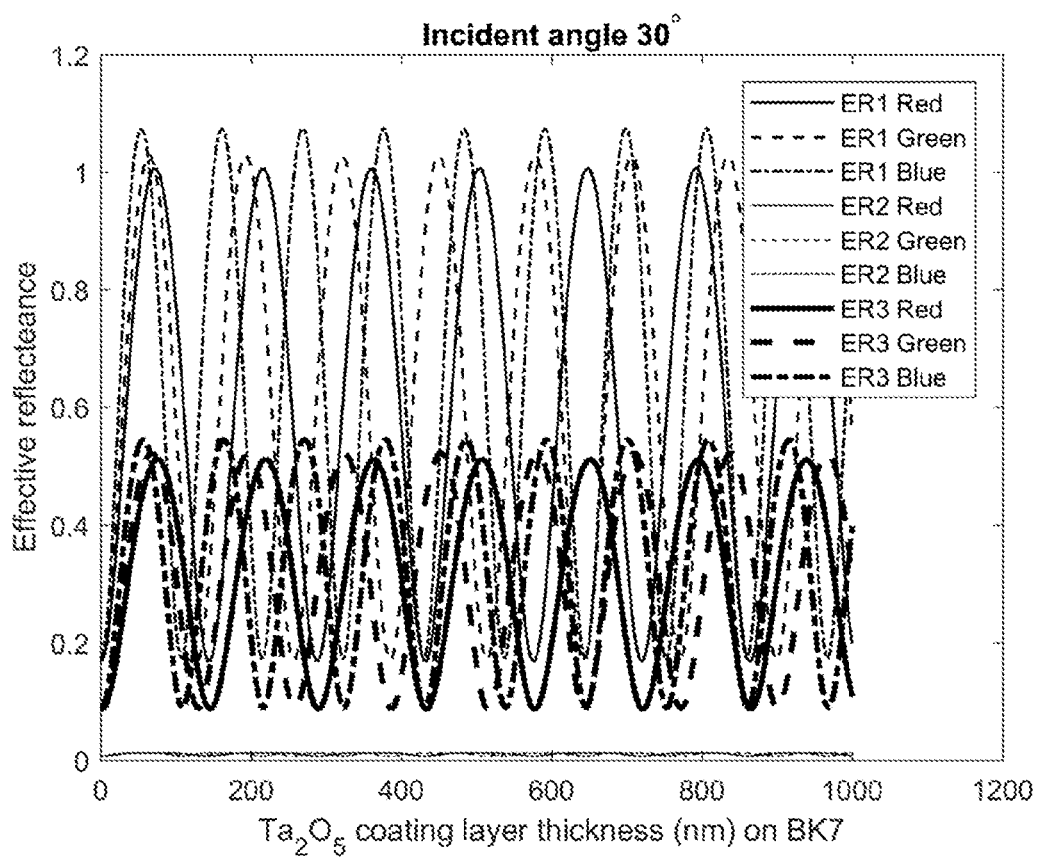
FIG. 13 is a representative effective reflectance plot of a three-detector system for a BK7 substrate coated with $Ta_2O_5$.

FIG. 13 is an effective reflectance plot of a three-detector system for a BK7 substrate coated with $Ta_2O_5$. It illustrates the $Ta_2O_5$ coating layer thickness dependence of the effective reflectance. The figure sets the incident angle of 30° as an example, and it assumes the same system parameters as in FIG. 12.

The aforementioned thickness, refractive index of the thin film and the refractive index of the substrate (n, d) or (n, d, $n_s$) retrieval can be calculated at each color channel, and experimentally, the average wavelength arrived at the detector of each color channel can be used for the analysis. Similar to the two-detector case, to resolve the ambiguity of periodic thickness dependence of the effective reflectance, two, or three, or even more color channels could be used. As shown in FIG. 12 and FIG. 13, the off-beat of different wavelengths will resolve the ambiguity of the thickness dependence and enable a unique thickness value retrieval in a much larger search range.

Similar to a two-detector system, for a Type 2 sample, the output irradiance values from these three detectors have to be subtracted from each other to get rid of the depolarized light contribution to the signal on the detector. After the mutual subtraction of the three effective reflectance values, only two independent optical parameters of the thin film coating could be retrieved. For example, the thickness and refractive index pairs (n, d) of a single layer thin film coating are retrievable, given a known refractive index $n_s$ of the substrate.

Mathematically, for a Type 2 sample, the data number DN of a pixel on the detector is proportional to the sum of the effective reflectance and the scattered depolarized light $$\frac{DN_1}{m_1} = ER_1 + S \tag{69}$$

$$\frac{DN_2}{m_2} = ER_2 + S \tag{70}$$

$$\frac{DN_3}{m_3} = ER_3 + S \tag{71}$$

The scattered light contribution S is the same for all detectors under the assumption that the depolarizing process of the depolarizing scatterer beneath the front surface is sufficient, such that the output from the depolarizing scatterer is approximately fully unpolarized.

After registration, mutually subtracting the three aligned detector images, $$\frac{DN_2 - DN_1}{m_{21}} = ER_2 - ER_1 \tag{72}$$

$$\frac{DN_3 - DN_1}{m_{31}} = ER_3 - ER_1 \tag{73}$$

$$\frac{DN_3 - DN_2}{m_{32}} = ER_3 - ER_2 \tag{74}$$

Similarly, the scaling factors $m_{21}$, $m_{31}$, and $m_{32}$ could be obtained from the calibration measurements with a reference phantom. If the data numbers of the corresponding pixels are $DN_{01}$, $DN_{02}$ and $DN_{03}$ for the reference, $$\frac{DN_{02} - DN_{01}}{m_{21}} = ER_{02} - ER_{01} \quad (75)$$

$$\frac{DN_{03} - DN_{01}}{m_{31}} = ER_{03} - ER_{01} \quad (76)$$

$$\frac{DN_{03} - DN_{02}}{m_{32}} = ER_{03} - ER_{02} \quad (77)$$

Applying the above general form to the previous exemplary setups, including two types of beamsplitter choices, following the same illumination and analyzer polarization choices, $$\frac{DN_2 - DN_1}{m_{21}} = 4r_p r_s \cos\Delta, \quad (78)$$

$$\frac{DN_3 - DN_1}{m_{31}} = 2r_p r_s (\sin\Delta + \cos\Delta), \quad (79)$$

$$\frac{DN_3 - DN_2}{m_{32}} = 2r_p r_s (\sin\Delta - \cos\Delta). \quad (80)$$

The three unknowns $r_p$, $r_s$, and $\Delta$ are determined by the thickness and refractive index of the thin film coating and the optical properties of the substrate.

Similarly, a lookup table of the mutual subtraction of effective reflectance sets ($ER_2-ER_1$, $ER_3-ER_1$, $ER_3-ER_2$) can be created for all possible combinations of the thickness and refractive index pairs (n, d). The thickness d and refractive index n of a single layer thin film coating can be determined by choosing the mutual subtraction of the effective reflectance set from the lookup table that has the smallest total discrepancy with the measured mutual subtraction of effective reflectance values.

The extra detector and another independent polarization analyzer in a three-detector system would enable one more unknown optical parameter determination. For example, for a Type 1 sample with a single-layer thin film coating, a three-detector system can measure both the thickness and refractive index of the thin film coating, and one more parameter, which could be the refractive index of an unknown substrate, or the extinction coefficient of the thin film coating if it is absorptive. As another example, if there are two layers in the thin film coating, and only the refractive index of one bottom coating layer is known, the three-detector system can measure the thickness and refractive index of the top coating layer and the thickness of the bottom coating layer.

Similar to a two-detector system, for the three-detector system and the following multiple-detector system, if the illumination light is not fully polarized, the process of mutual subtraction of the effective reflectances and the calibration of the reference phantom will minimize the error caused by the increase of the degree of polarization of the unpolarized part of the original illumination after reflection. Since mutual subtraction of the effective reflectance is employed in the process, there will be no difference for Type 1 samples and Type 2 samples. The number of retrievable optical parameters will follow the previous analysis of Type 2 samples.

For a multiple-detector system as shown in FIG. 8, if in total there are q detectors and q−1 beamsplitters, similar to the three-detector system, the general form of Jones calculus can be summarized as $$E_{ok} = A_k F_k B_k I \Phi_2 R \Phi_1 E_i \quad (81)$$

where k=1, 2, . . . q, i.e. positive integers up to q. and $B_k$ is a 2×2 matrix, the product of individual beamsplitter matrices in a corresponding light path, and the components could be either reflection or transmission beamsplitter matrix. Alternatively, the q optical branches can be generated with one or more diffractive beamsplitter with q main diffraction orders in use. The rest of the notations carry correspondingly similar meanings as described before.

Following similar simplification procedure as in the three-detector system, with the calibration of the reference phantom, the above electric field output could be simplified as $$E_{ok} = A_k B_k R E_i \quad (82)$$

In the specific case where all the beamsplitters in the system are 50:50 equal-splitting beamsplitters, the above results could be further simplified as $$E_{ok} = A_k B^{nb} R E_i \quad (83)$$

where B denotes the ideal equal-splitting, non-polarizing beamsplitter matrix of $$B = \frac{\sqrt{2}}{2}\begin{bmatrix} 1 & 0 \\ 0 & 1 \end{bmatrix}$$

and nb denotes the number of beamsplitters in the optical path before the light reaches a detector, and $1 \leq nb \leq q-1$.

The analyzers polarization states are independent to each other. The absolute reflectance values are calculated as $$AER_k = |E_{ok}|^2 \quad (84)$$

The beamsplitter compensating factor due to the unequal splitting ratio and/or the unequal number of beamsplitters in different optical paths is $S_{Bk}$. For a diffractive beamsplitter, the beamsplitter compensating factors are determined by the diffraction efficiencies of the orders in use. For the specific case where all the beamsplitters are 50:50 beamsplitters, $S_{Bk} = 2^{nb-1}$. The effective reflectance values are $$ER_k = c \times S_{Bk} \times AER_k \quad (85)$$

where c is an appropriately chosen constant to simplify the mathematical form of the effective reflectance. c remains the same value for all detectors.

For Type 1 samples, where the reflection from the front surface is dominant, scaling factors are used to convert from the data number experimentally measured at each corresponding pixel of each detector to the effective reflectance values $$ER_k = \frac{DN_k}{m_k} \quad (86)$$

The scaling factors are calculated after the calibration process with a reference phantom with known optical properties of the same or at least similar shape of the sample under test $$m_k = \frac{DN_{0k}}{ER_{0k}} \quad (87)$$

For Type 2 samples, where there is a depolarizing element underneath the front surface, the data number represents both the reflected light from the front surface and the scattered light from the depolarizing element $$\frac{DN_k}{m_k} = ER_k + S \quad (88)$$

If the depolarizing element scatters light sufficiently, the light output could be approximated as completely unpolarized light and therefore, S will remain a constant regardless of the analyzer polarization state. By mutually subtracting these detector signals $$\frac{DN_k - DN_j}{m_{kj}} = ER_k - ER_j \quad (89)$$

where k and j are both positive integers in the range from 1 to q, and k≠j. To avoid counting the equivalent subtractions twice, k>j can be further limited.

Similar to previously described calibration process for Type 1 samples, the scaling factors can be calculated from a reference phantom with known optical properties $$m_{kj} = \frac{DN_{0k} - DN_{0j}}{ER_{0k} - ER_{0j}} \quad (90)$$

To extract the optical parameters of the thin film coating, for example, if there are p unknowns $(x_1, x_2, \ldots, x_p)$, p≤q, where these unknown optical parameters could be but are not limited to thicknesses or refractive indices of some sublayers in the thin film coating. A lookup table with all the unknown parameters each set in a properly chosen search range could be created, so that $x_1 \in [x_{11}, x_{12}]$, $x_2 \in [x_{21}, x_{22}], \ldots, x_p \in [x_{p1}, x_{p2}]$.

For Type 1 samples with fully polarized illumination light, the effective reflectances of all possible combinations of these unknown parameters are calculated for each color channel of the detector. A subsequent comparison of these experimentally measured effective reflectance values of each color channel of the detector with this lookup table of effective reflectance data will locate a set of optical parameters $(x_1, x_2, \ldots, x_p) = (x_{10}, x_{20}, \ldots, x_{p0})$ that generates the least discrepancy in all the ER values with the experimental data. These unknown parameters are therefore retrieved.

For Type 1 samples with partially polarized illumination and Type 2 samples with fully polarized or partially polarized illumination light, the mutual subtraction of effective reflectances, $ER_k - ER_j$, of all possible combinations of these unknown parameters are calculated for each color channel of the detector. Up to q−1 unknown parameters could be retrieved due to the mutual subtraction. A subsequent comparison of the experimentally measured mutual subtraction of effective reflectance values of each color channel of the detector with this lookup table will locate a set of optical parameters $(x_1, x_2, \ldots, x_p) = (x_{10}, x_{20}, \ldots, x_{p0})$, that generates the least discrepancy in all the mutual subtraction of effective reflectance values with the experimental data. These unknown parameters are therefore retrieved.

The invention has been described in detail with particular reference to certain preferred embodiments thereof, but it will be understood that variations and modifications can be effected within the spirit and scope of the invention.

What is claimed is:

1. A thin film analysis apparatus, comprising:
    an illuminator for providing illumination light to an extended area of a sample, wherein said sample has a geometrical shape;
    an imaging group to receive reflected light from said extended area of said sample;
    at least one non-polarizing beamsplitter to receive said reflected light from said imaging group and split said reflected light into more than one optical branch;
    at least two analyzers, one for receiving one of said more than one optical branch from said beamsplitter and analyzing a polarization state thereof, wherein each of said at least two analyzers is located between one of said at least one beamsplitter and a detector;
    at least two detectors, one for receiving one of said more than one optical branch from one of said at least two analyzers to generate and record image series of a surface of said extended area of said sample, wherein one detector is aligned uniquely with one of said at least two analyzers; and
    a reference phantom with known optical properties to replace said sample for calibration, wherein said reference phantom has the same or substantially similar geometrical shape as of said sample or a segment of said sample.

2. The apparatus of claim 1, wherein said illuminator comprises an array of individual broadband light sources, a diffusing structure, and a polarizer structure.

3. The apparatus of claim 2, wherein said diffusing structure is one or more layers of diffusing materials.

4. The apparatus of claim 1, wherein said sample has a thin film that dynamically evolves and said detectors are substantially synchronized so that said image series are aligned in time sequence to minimize analysis error.

5. The apparatus of claim 1, wherein said sample is flat, curved or has a freeform shape that decomposes into measurable flat or curved segments.

6. The apparatus of claim 1, wherein said sample is attached to a support to adjust a position of said sample.

7. The apparatus of claim 1, wherein said detectors are charge-coupled devices (CCD), or complementary metal oxide semiconductor (CMOS).

8. The apparatus of claim 1, wherein said analyzers have different polarization orientations.

9. The apparatus of claim 1, further comprising a processor or a computer connected to said detectors to store and analyze said images series.

10. The apparatus of claim 1, further comprising at least one image output system to display said image series.

11. The apparatus of claim 1, further comprising a registration illumination system located between said sample and said imaging group.

12. The apparatus of claim 11, wherein a center of said registration illumination system is substantially aligned with an optical axis of said imaging group.

13. The apparatus of claim 11, wherein said registration illumination system comprises three or more light sources or a circular ring light source.

14. The apparatus of claim 1, further comprising focusing groups each located between one of said at least one non-polarizing beamsplitter and one of said at least two analyzers.

15. A method of analyzing a thin film over an extended area of a sample, said method comprising the steps of:
    illuminating an extended area of a sample having a geometrical shape with at least partially polarized illumination light;

directing light reflected off said sample to pass through, in order, a registration illumination system, an imaging group, at least one non-polarizing beamsplitter, and at least two analyzers and at least two detectors, wherein one of said analyzers is aligned with one of said detectors;

capturing and recording a sample image series with each of said detectors;

differentiating said sample into different types;

aligning image series of said detectors by matching a reflected image of said registration illumination system on each detector;

replacing said sample with a reference phantom with known optical properties, which has the same or substantially similar geometrical shape as of said sample or a segment of said sample to record an image series of said reference phantom with each of said detectors;

resizing the image series of said reference phantom to match the sample image series, based on the reflected images of said registration illumination system;

calculating beamsplitter compensating factors due to an unequal splitting ratio and an unequal number of beamsplitters in different optical paths;

selecting a search range for unknown optical parameters of said sample;

calculating scaling factors based on the type of said sample and a degree of polarization of said at least partially polarized illumination light, and determining the unknown optical parameters.

16. The method of claim 15, wherein differentiating the sample into different types comprises differentiating into two sample types:

Type 1 samples having a dominant reflection from a front surface, and no strong reflection from all other optical surfaces or structures beneath said front surface; and Type 2 samples having a transparent or semi-transparent front surface, with a depolarizing element beneath said front surface.

17. The method of claim 16, wherein said sample is a Type 1 sample under fully polarized illumination light, wherein said method further comprising the steps of:

calculating scaling factors that quantify the proportionality of data numbers of said image series of said reference phantom and effective reflectances of said reference phantom;

calculating effective reflectances of said sample, based on said scaling factors calculated from said reference phantom;

creating a lookup table of effective reflectances of all possible combinations of the unknown optical parameters of said sample in said search range;

comparing the effective reflectances of said sample with said lookup table, and selecting a set of optical parameters that generates the least discrepancy with the effective reflectances of said sample to determine the unknown parameters.

18. The method of claim 16, wherein said sample is a Type 1 sample under partially polarized illumination light, or a Type 2 sample under at least partially polarized illumination light, wherein said method further comprising the steps of:

calculating scaling factors that quantify the proportionality of the mutual subtraction of data numbers of said image series of said reference phantom and the mutual subtraction of effective reflectances of said reference phantom;

calculating the mutual subtraction of effective reflectances of said sample, based on said scaling factors calculated from said reference phantom;

creating a lookup table of the mutual subtraction of effective reflectances of all possible combinations of the unknown optical parameters of said sample in said search range;

comparing the mutual subtraction of the effective reflectances of said sample with said lookup table, and selecting a set of optical parameters that generates the least discrepancy with the mutual subtraction of the effective reflectances of said sample to determine the unknown parameters.

19. The method of claim 16, wherein said depolarizing element in a Type 2 sample scatters light sufficiently, wherein the output light from said depolarizing element is unpolarized light.

* * * * *